(12) United States Patent
Towner et al.

(10) Patent No.: US 10,030,076 B2
(45) Date of Patent: Jul. 24, 2018

(54) ANTIBODIES AGAINST GLIOMA BIOMARKERS

(71) Applicant: OKLAHOMA MEDICAL RESEARCH FOUNDATION, Oklahoma City, OK (US)

(72) Inventors: Rheal Towner, Piedmont, OK (US); Jonathan Wren, Norman, OK (US)

(73) Assignee: OKLAHOMA MEDICAL RESEARCH FOUNDATION, Oklahoma City, OK (US)

( * ) Notice: Subject to any disclaimer, the term of this patent is extended or adjusted under 35 U.S.C. 154(b) by 0 days.

(21) Appl. No.: 15/109,462

(22) PCT Filed: Jan. 6, 2015

(86) PCT No.: PCT/US2015/010355
§ 371 (c)(1),
(2) Date: Jul. 1, 2016

(87) PCT Pub. No.: WO2015/105806
PCT Pub. Date: Jul. 16, 2015

(65) Prior Publication Data
US 2017/0008969 A1 Jan. 12, 2017

Related U.S. Application Data

(60) Provisional application No. 61/924,480, filed on Jan. 7, 2014.

(51) Int. Cl.
| | |
|---|---|
| *C07K 16/22* | (2006.01) |
| *C07K 16/18* | (2006.01) |
| *A61K 39/395* | (2006.01) |
| *C07K 16/30* | (2006.01) |
| *C07K 16/24* | (2006.01) |
| *C07K 16/28* | (2006.01) |
| *G01N 33/574* | (2006.01) |
| *A61K 45/06* | (2006.01) |
| *C12Q 1/6886* | (2018.01) |
| *A61K 39/00* | (2006.01) |

(52) U.S. Cl.
CPC .... *C07K 16/3053* (2013.01); *A61K 39/39558* (2013.01); *A61K 45/06* (2013.01); *C07K 16/18* (2013.01); *C07K 16/22* (2013.01); *C07K 16/24* (2013.01); *C07K 16/28* (2013.01); *C07K 16/2803* (2013.01); *C07K 16/2863* (2013.01); *C12Q 1/6886* (2013.01); *G01N 33/57407* (2013.01); *A61K 2039/505* (2013.01); *C07K 2317/24* (2013.01); *C07K 2317/76* (2013.01); *C12Q 2600/158* (2013.01); *G01N 2333/47* (2013.01); *G01N 2333/705* (2013.01)

(58) Field of Classification Search
CPC .... C07K 16/3053; C07K 16/22; C07K 16/18; A61K 39/395

USPC .................................................... 424/130.1
See application file for complete search history.

(56) References Cited

U.S. PATENT DOCUMENTS

2009/0068202 A1  3/2009 Chen et al.

FOREIGN PATENT DOCUMENTS

WO    WO 2008/055889    5/2008

OTHER PUBLICATIONS

Neurosurgery_ Towner et al. (Neurosurgery, vol. 72, Issue 1, Jan. 1, 2013, pp. 77-91).*
Agrawal and Lynskey, "Candidate genes for cannabis use disorders: findings, challenges and directions," *Addiction*, 104: 518-32, 2009.
Agrawal et al., "An autosomal linkage scan for cannabis use disorders in the nicotine addiction genetics project,"*Arch Gen Psychiatry*, 65: 713-21, 2008.
Alizadeh and Staudt, "Genomic-scale gene expression profiling of normal and malignant immune cells," *Current Opinion in Immunology*, 12:219-225, 2000.
Alizadeh et al., "Distinct types of diffuse large B-cell lymphoma identified by gene expression profiling," *Nature*, 403:503-511, 2000.
Bittner et al., "Molecular classification of cutaneous malignant melanoma by gene expression profiling," *Nature*, 406:536-540, 2000.
Cheng et al., "Fibulin 1 is downregulated through promoter hypermethylation in gastric cancer," *Br J Cancer*, 99:2083-7, 2008.
Davidson et al., "Gene expression signatures differentiate ovarian/peritoneal serous carcinoma from breast carcinoma in effusions," *J Cell Mol Med*, 15:535-44, 2011.
Flynn et al., "Hypoxia-regulated protein expression, patient characteristics, and preoperative imaging as predictors of survival in adults with glioblastoma multiforme," *Cancer*, 113:1032-42, 2008.
Gillespie et al., "Silencing of HIF-1alpha by RNA interference in human glioma cells in vitro and in vivo," *Methods Mol Biol*, 487:283-301, 2009.
Gillespie et al., "Silencing of hypoxia inducible factor-1alpha by RNA interference attenuates human glioma cell growth in vivo,"*Clin Cancer Res*, 13:2441-8, 2007.
Golub et al., "Molecular classification of cancer: class discovery and class prediction by gene expression monitoring," *Science*, 286:531-537, 1999.
Gyorffy et al., "A snapshot of microarray-generated gene expression signatures associated with ovarian carcinoma," *Int J Gynecol Cancer*, 18:1215-33, 2008.

(Continued)

*Primary Examiner* — Yan Xiao
(74) *Attorney, Agent, or Firm* — Parker Highlander PLLC

(57) ABSTRACT

The present disclosure is directed to antibodies binding to ELTDI. Plexin-B2, Spondin-1, fibulin-1, LINGO I or SLIT3 and methods of using such antibodies to treat and/or diagnose gliomas. Thus, in accordance with the present disclosure, there is provided a method of inhibiting a glioma cell comprising contacting said glioma cell with a first antibody or antibody fragment that binds immunologically to ELTDI, Plexin-B2, Spondin-1 or SLIT3. The method may further comprise contacting said glioma cell with a second anti-cancer agent or treatment.

19 Claims, 17 Drawing Sheets
(10 of 17 Drawing Sheet(s) Filed in Color)

(56) References Cited

OTHER PUBLICATIONS

Jensen et al., "Inhibition of hypoxia inducible factor-1 alpha (HIF-1alpha) decreases vascular endothelial growth factor (VEGF) secretion and tumor growth in malignant gliomas,"*J. Neurooncol*, 78:233-47, 2006.

Jensen, "Hypoxia in the tumorigenesis of gliomas and as a potential target for therapeutic measures," *Neurosurg Focus*, 20(4):E24, 2006.

Kanda et al., "Promoter hypermethylation of fibulin 1 gene is associated with tumor progression in hepatocellular carcinoma," *Mol Carcinog.*, 50:571-9, 2011.

Katoh and Katoh, "Comparative genomics on SLIT1, SLIT2, and SLIT3 orthologs," *Oncol Rep*, 14:1351-5, 2005.

Kobel et al., "Ovarian carcinoma subtypes are different diseases: implications for biomarker studies,"*PLoS Med*, 5:e232, 2008.

Lin and Chuang, "Genes responsible for the characteristics of primary cultured invasive phenotype hepatocellular carcinoma cells," *Biomed Pharmacother.*, 66:454-8, 2012.

Masiero et al., "A core human primary tumor angiogenesis signature identifies the endothelial orphan receptor ELTD1 as a key regulator of angiogenesis," *Cancer Cell*, 24:229-41, 2013.

Medioni et al., "Expression of Slit and Robo genes in the developing mouse heart," *Dev. Dyn.*, 239:3303-11, 2010.

Nechiporuk et al., "ETL, a novel seven-transmembrane receptor that is developmentally regulated in the heart. ETL is a member of the secretin family and belongs to the epidermal growth factor-seven-transmembrane subfamily," *J. Biol Chem*, 276: 4150-7, 2001.

PCT International Search Report and Written Opinion issued in International Application No. PCT/US2015/010355, dated Jul. 2, 2015.

PCT Invitation to Pay Additional Fees issued in International Application No. PCT/US2015/010355, dated Apr. 14, 2015.

Phillips et al., "Molecular subclasses of high-grade glioma predict prognosis, delineate a pattern of disease progression, and resemble stages in neurogenesis," *Cancer Cell*, 9:157-73, 2006.

Porto Neto et al., "DNA variation in the gene ELTD1 is associated with tick burden in cattle," *Anim Genet*, 42: 50-5, 2011.

Pupa, et al., "Immunological and pathobiological roles of fibulin-1 in breast cancer," *Oncogene*, 23:2153-60, 2004.

Ragel et al., "Identification of hypoxia-induced genes in a malignant glioma cell line (U-251) by cDNA microarray analysis,"*Neurosurg Rev.*, 30:181-7; discussion 187, 2007.

Rong et al., "Early growth response gene-1 regulates hypoxia-induced expression of tissue factor in glioblastoma multiforme through hypoxia-inducible factor-1-independent mechanisms," *Cancer Res.*, 66:7067-74, 2006.

Towner et al., "ELTD1, a potential new biomarker for gliomas," *Neurosurgery*, 72(1):77-90, 2013.

Towner et al., "Experimental validation of 5 in-silico predicted glioma biomarkers," *Neuro Oncol.*, 15(12):1625-1634, 2013.

Verhaak et al., "Integrated genomic analysis identifies clinically relevant subtypes of glioblastoma characterized by abnormalities in PDGFRA, IDH1, EGFR, and NF1," *Cancer Cell*, 17:98-110, 2010.

Wallgard et al., "Identification of a core set of 58 gene transcripts with broad and specific expression in the microvasculature,"*Arterioscler Thromb Vasc Biol.*, 28(8):1469-76, 2008.

Wen et al., "GROalpha is highly expressed in adenocarcinoma of the colon and down-regulates fibulin-1," *Clin Cancer Res*, 12:5951-9, 2006.

Wlazlinski et al., "Downregulation of several fibulin genes in prostate cancer," *Prostate*, 67:1770-80, 2007.

Wren, "A global meta-analysis of microarray expression data to predict unknown gene functions and estimate the literature-data divide," *Bioinformatics*, 25:1694-701, 2009.

Ziegler et al., "ELTD1, an effective anti-angiogenic target for gliomas: preclinical assessment in mouse GL261 and human G55 xenograft glioma models," *Neuro-Oncology*, doi:10.1093/neuonc/now147, 11 pages, first published online Jul. 14, 2016.

Extended European Search Report issued in European Patent Application No. 15734930.9, dated Jul. 4, 2017.

Hernandez-Pedro et al., "An update in the use of antibodies to treat glioblastoma multiforme," *Autoimmune Diseases*, vol. 2013, pp. 1-14, Jan. 1, 2013.

* cited by examiner

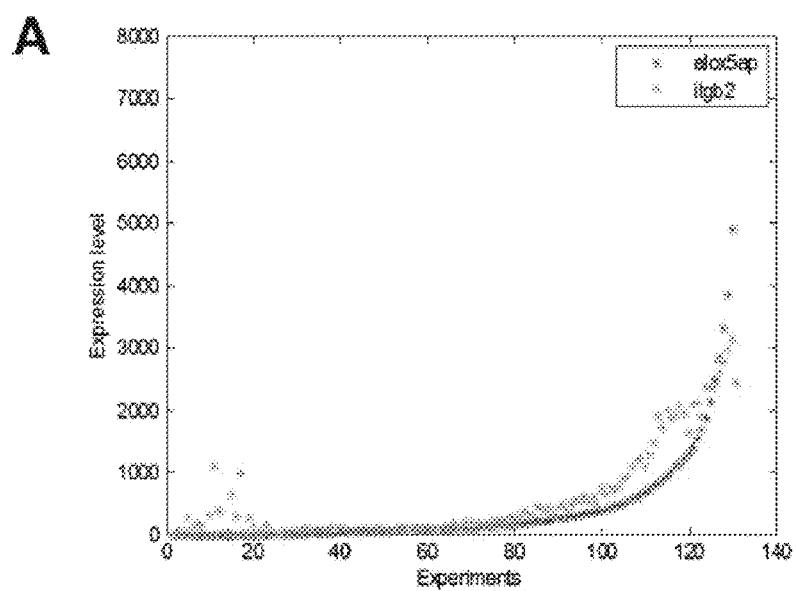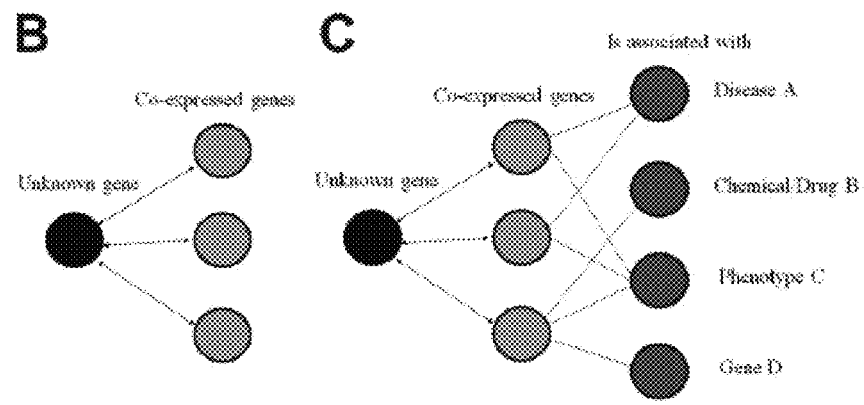
FIGS. 1A-C

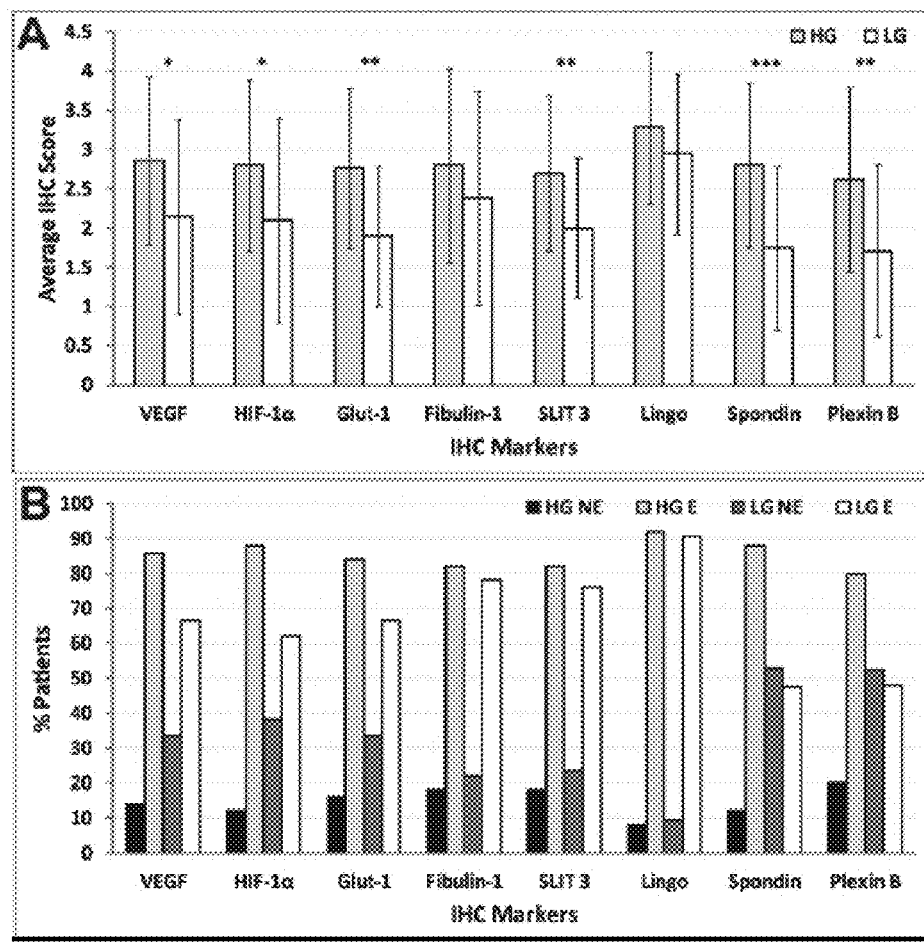
FIGS. 2A-B

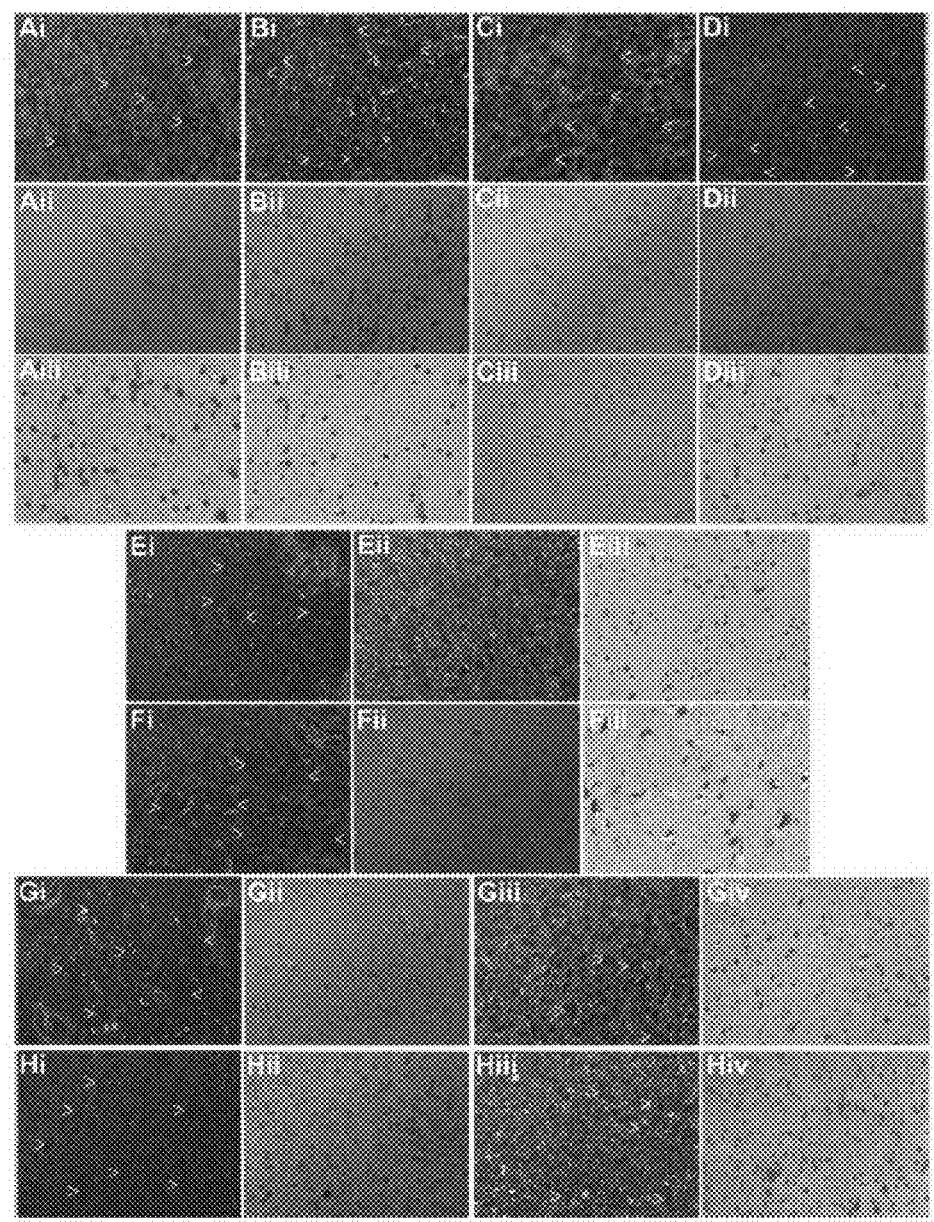
FIGS. 3Ai-Hiii

FIGS. 5Ai-Eiv

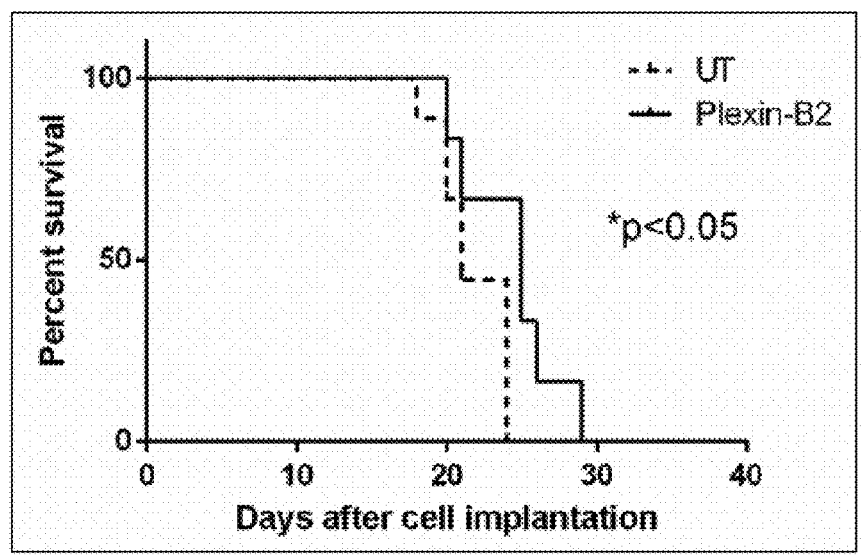
FIG. 16
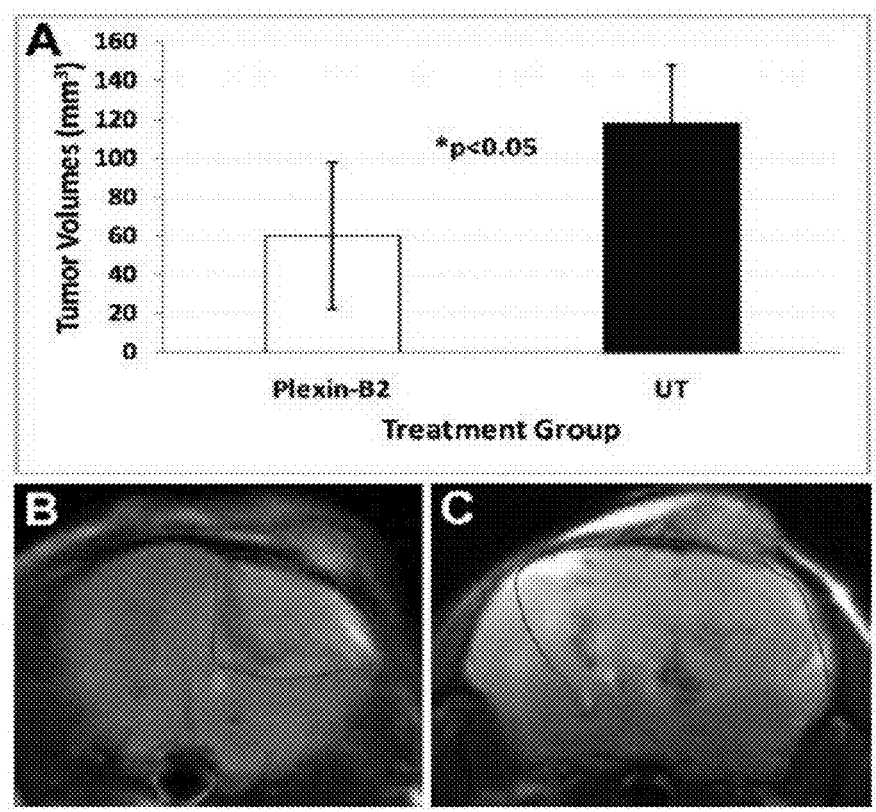
FIGS. 17A-C

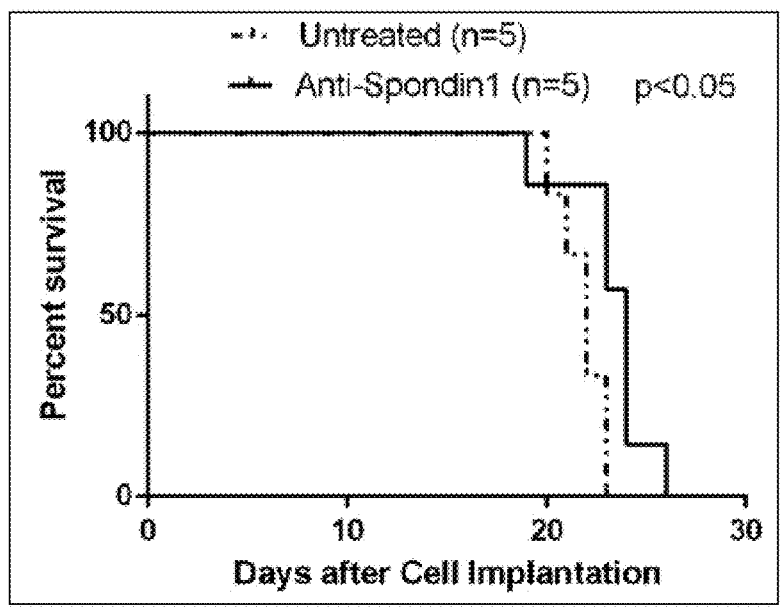
FIG. 18
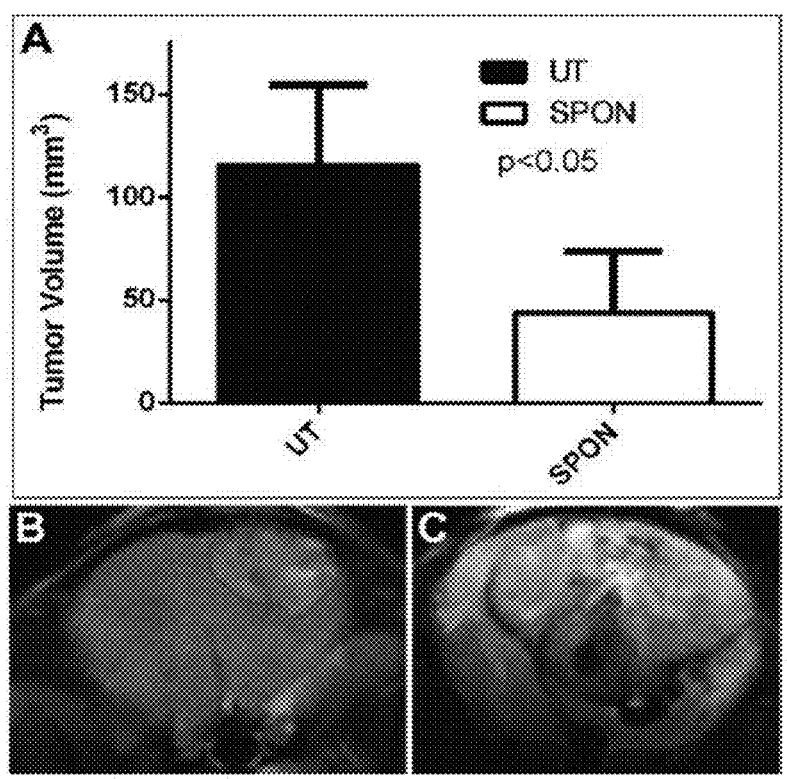
FIGS. 19A-C

ANTIBODIES AGAINST GLIOMA BIOMARKERS

The present application is a national phase application under 35 U.S.C. § 371 of International Application No. PCT/US2015/010355, filed Jan. 6, 2015, which claims benefit of priority to U.S. Provisional Application Ser. No. 61/924,480, filed Jan. 7, 2014, the entire contents of each of the above-referenced disclosures are hereby incorporated by reference.

FEDERAL FUNDING CLAUSE

This invention was made with government support under grant number 5P20GM103636-02 awarded by the National Institutes of Health. The government has certain rights in the invention.

BACKGROUND

1. Field

The present disclosure relates generally to the fields of medicine, oncology and immunotherapeutics. More particularly, it concerns the development of immunoreagents for use in treating gliomas.

2. Background

Gliomas are complex cancers with different growth characteristics and involve different types of cells. Because the original clone of tumor cells may exist at any stage during the cell differentiation, the boundaries between cell lineages can be blurred. The current morphologically-based tumor classifications often mix cell lineage features with tumor growth characteristics. The results are subjective and there can be disagreements among physicians as to what kind of tumor cell is involved. To date, a successful application of gene-based classification has not been applied to gliomas.

Molecular biology provides the potential for an improved method of tumor cell classification. This is based on the premise that all cell phenotypes have their origin in genetics. Thus, the rationale is that a detailed examination of gene expression will be the most accurate representation of a cell's character. Recent successes in the subclassification of neoplasms within a disease group using gene expression profiles provide support for such a belief (Golub et al., 1999; Alizadeh et al., 2000; Bittner et al., 2000).

Thus, the issue is how to best identify the "strong" feature genes that are closely linked to specific phenotypes from among the thousands of genes in gene expression profiles, and whether this information really aids classification of tumors more. There are many technical challenges in the path to accomplishing the task of finding the key links. Algorithms can assist in the identification of robust classifiers from very limited data sets. Three criteria have to be met: (a) given a set of variables, a classifier from the sample data should provide good classification over the general population; (b) the analysis should be able to estimate the error of a designed classifier when data are limited; and (c) given a large set of potential variables, the analysis should be able to select a set of variables as inputs to the classifier from the large number of expression level determinations provided by microarrays.

However, a major roadblock is the small sample size issue inherent to microarray-based classification efforts (Dougherty, 2001). Contributing to this are the limited numbers of human tissues for study and the cost of such gene expression profiling projects. Because classifiers are designed from observed expression vectors that have randomness arising from variability, both biologic and experimental, the design, performance evaluation, and application of classifiers must take this randomness into account, especially when the number of samples (tissue specimens) is small, which is the case in most human tissue-based microarray studies.

SUMMARY

Thus, in accordance with the present disclosure, there is provided a method of inhibiting a glioma cell comprising contacting said glioma cell with a first antibody or antibody fragment that binds immunologically to ELTD1, Plexin-B2, Spondin-1 or SLIT3. The method may further comprise contacting said glioma cell with a second anti-cancer agent or treatment. The second anti-cancer agent or treatment maybe selected from chemotherapy, radiotherapy, immunotherapy, hormonal therapy, or toxin therapy. The second anti-cancer agent or treatment may be given at the same time as said antibody or antibody fragment, or before and/or after said antibody or antibody fragment. The second agent may be an anti-VEGF antibody, an anti-EGFR antibody or an anti-c-Met antibody. The second agent may be a second anti-ELTD1 antibody, anti-Plexin-B2 antibody, anti-Spondin-1 antibody or anti-SLIT3 antibody distinct first antibody or antibody fragment. The glioma cell cel may be a metastatic glioma cell, a multiply drug resistant glioma cell or a recurrent glioma cell.

The antibody may be is a single chain antibody or a chimeric antibody. The antibody fragment may be a Fab fragment or a single domain antibody. The antibody or antibody fragment may be a murine antibody, a human antibody, an IgG, a murine IgG antibody, a human IgG antibody, a humanized antibody or a humanized IgG antibody. The antibody or antibody fragment may further comprise an antitumor drug linked thereto, such as linked through a photolabile linker. The antitumor drug may alternatively be linked through an enzymatically-cleaved linker. The antitumor drug may be a toxin, a radioisotope, a cytokine, or an enzyme. The antibody or antibody fragment may further comprise a label, such as a peptide tag, an enzyme, a magnetic particle, a chromophore, a fluorescent molecule, a chemilluminescent molecule, or a dye. The antibody or antibody fragment may be conjugated to a liposome or nanoparticle. The antibody or antibody fragment results in the induction of cell death, such as by antibody-dependent cell cytotoxicity or complement-mediated cytotoxcity.

In another embodiment, there is provided a method of treating glioma in a subject comprising administering to said subject an antibody or antibody fragment that binds immunologically to ELTD1, Plexin-B2, Spondin-1 or SLIT3. The method may further comprise contacting said glioma cell with a second anti-cancer agent or treatment. The second anti-cancer agent or treatment maybe selected from chemotherapy, radiotherapy, immunotherapy, hormonal therapy, or toxin therapy. The second anti-cancer agent or treatment may be given at the same time as said antibody or antibody fragment, or before and/or after said antibody or antibody fragment. The second agent may be an anti-VEGF antibody, an anti-EGFR antibody or an anti-c-Met antibody. The second agent may be a second anti-ELTD1 antibody, anti-Plexin-B2 antibody, anti-Spondin-1 antibody or SLIT3 antibody distinct first antibody or antibody fragment. The glioma cell cel may be a metastatic glioma cell, a multiply drug resistant glioma cell or a recurrent glioma cell.

The antibody may be is a single chain antibody or a chimeric antibody. The antibody fragment may be a Fab fragment or a single domain antibody. The antibody or antibody fragment may be a murine antibody, a human antibody, an IgG, a murine IgG antibody, a human IgG antibody, a humanized antibody or a humanized IgG antibody. The antibody or antibody fragment may further comprise an antitumor drug linked thereto, such as linked through a photolabile linker. The antitumor drug may alternatively be linked through an enzymatically-cleaved linker. The antitumor drug may be a toxin, a radioisotope, a cytokine, or an enzyme. The antibody or antibody fragment may further comprise a label, such as a peptide tag, an enzyme, a magnetic particle, a chromophore, a fluorescent molecule, a chemilluminescent molecule, or a dye. The antibody or antibody fragment may be conjugated to a liposome or nanoparticle. The antibody or antibody fragment results in the induction of cell death, such as by antibody-dependent cell cytotoxicity or complement-mediated cytotoxcity.

The antibody or antibody may be fragment is administered more than once, such as administered daily, every other day, every three days, every four days, every five days, every six days, twice weekly, weekly, every two weeks, every three weeks or monthly. The antibody or antibody fragment may be administered local to the tumor or regional to said tumor, or administered systemically, intratumorally, intravenously, intra-arterially or intracranially.

In still another embodiment, there is provided a method of detecting a glioma in a subject comprising (a) administering to said subject a first antibody or antibody fragment that binds immunologically to spondin 1, Plexin-B2, SLIT3, fibulin-1 or LINGO1, wherein said antibody is conjugated to a detectable agent; and (b) detecting said antibody or antibody fragment bound to a glioma in said subject. The method may comprises administering a second antibody or antibody fragment that binds to ELTD1, spondin 1, Plexin-B2, SLIT3, fibulin-1 or LINGO1, but not to the same antigen as said first antibody. The agent may be a peptide tag, an enzyme, a magnetic particle, a chromophore, a fluorescent molecule, an MRI contrast agent, a chemilluminescent molecule, a radioisotope or a dye. The subject may be suspected of having, or known to have, a glioma. The antibody may be is a single chain antibody or a chimeric antibody. The antibody fragment may be a Fab fragment or a single domain antibody. The antibody or antibody fragment may be a murine antibody, a human antibody, an IgG, a murine IgG antibody, a human IgG antibody, a humanized antibody or a humanized IgG antibody.

In still yet a further embodiment, there is provided a method of diagnosing a glioma in a subject comprising (a) administering to said subject a first antibody or antibody fragment that binds immunologically to spondin 1, Plexin-B2, SLIT3, fibulin-1 or LINGO1, wherein said antibody is conjugated to a detectable agent; and (b) detecting said antibody or antibody fragment bound to a tissue site in said subject, wherein the presence of bound antibody to said tissue site diagnoses said subject has having glioma. The method may comprise administering a second antibody or antibody fragment that binds to ELTD1, spondin 1, Plexin-B2, SLIT3, fibulin-1 or LINGO1, but not to the same antigen as said first antibody. The agent may be a peptide tag, an enzyme, a magnetic particle, a chromophore, a fluorescent molecule, an MRI contrast reagent, a chemilluminescent molecule, a radioisotope or a dye. The subject may be suspected of having glioma.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

The patent or application file contains at least one drawing executed in color. Copies of this patent or patent application publication with color drawing(s) will be provided by the Office upon request and payment of the necessary fee.

FIGS. 1A-C: The global microarray meta-analysis (GAMMA) bioinformatics approach. (FIG. 1A) For all human genes, the first step is to identify their coexpression trends. Previous experiments show that genes positively correlated in their coexpression levels tend to be related by function, phenotype, and disease relevance. For example, for every experiment where 2 genes, alox5ap and itgb2, are expressed, this is quantified by Pearson correlation; however, not all genes have expression data. (FIG. 1B) For genes of unknown function, the second step is to identify the 20 genes with the strongest coexpression correlation. In this example, only 3 genes are shown for simplicity. (FIG. 1C) The third step is to identify what the coexpressed genes have in common Text-mining software (IRIDESCENT) is used to analyze what diseases, phenotypes, chemicals, and other genes appear in the literature with each of the coexpressed genes. These are the inferred associations for the unknown gene. The set of coexpressed genes is searched for reported commonalities in the peer-reviewed literature. After all of the genes are analyzed, the list is shortened to include those with certain characteristics. In this example, the inventors only include those that are inferred to be associated with gliomas, are plasma-membrane bound, and have commercial antibodies available for validation experiments to be conducted to establish whether these proteins are differentially present in gliomas.

FIGS. 2A-B: Spondin1, SLIT3, and Plexin-B2 levels are higher in high-grade (HG) gliomas compared with the levels in low-grade (LG) gliomas. (FIG. 2A) Graph showing average IHC scores for biomarkers (vascular endothelial growth factor (VEGF), hypoxia inducible factor 1-α (HIF-1α), glucose transporter-1 (GLUT-1), Fibulin-1, SLIT3, Spondin1, Lingo1, or Plexin-B2) in high-grade gliomas (50 patients; 21 female, and 29 male) and low-grade gliomas (21 patients; 10 female, and 11 male). Scores were obtained using the following grading criteria: 0: 0%; 1: 0 to <25%; 2: 25 to <50%; 3: 50 to <75%; 4: 75-100% detection of IHC stain. Significant differences in marker levels between HG and LG was established when *$p<0.05$, **$p<0.01$, or

***p<0.001. Actual p-values for each biomarker are: 0.0161 for VEGF, 0.0227 for HIF-1α, 0.0013 for Glut-1, 0.2081 for Fibulin-1, 0.0069 for SLIT3, 0.2054 for Lingo1, 0.0004 for Spondin1 and 0.0035 for Plexin-B2. (FIG. 2B) Graph showing the percentage of patients that expressed biomarkers stained by IHC in high-grade gliomas (50 patients) and low-grade gliomas (21 patients). A negative expression (NE) result was attributed to IHC scores of 0 or 1. A positive expression (E) result was attributed to IHC scores of 2-4.

FIGS. 3Ai-Hiv: VEGF, HIF-1α, GLUT-1, SLIT3, Spondin1, and Plexin-B2 levels are elevated in high-grade gliomas compared with low-grade gliomas. (FIGS. 3Ai-iii) Representative IHC staining for VEGF in a GBM (FIG. 3Ai), an oligodendroglioma (FIG. 3Aii), and normal brain (FIG. 3Aiii). (FIGS. 3Bi-iii) Representative IHC staining for HIF-1a in a GBM (FIG. 3Bi), a low-grade astrocytoma (LGA) (FIG. 3Bii), and normal brain (FIG. 3Biii). (FIGS. 3Ci-iii) Representative IHC staining for GLUT-1 in a GBM (FIG. 3Ci), an oligodendroglioma (FIG. 3Cii), and normal brain (FIG. 3Ciii). (FIGS. 3Di-iii) Representative IHC staining for SLIT3 in a GBM (FIG. 3Di), an LGA (FIG. 3Dii), and normal brain (FIG. 3Diii). (FIGS. 3Ei-iii) Representative IHC staining for spondin1 in a GBM (FIG. 3Ei), an LGA (FIG. 3Eii), and normal brain (FIG. 3Eiii). (FIGS. 3Fi-iii) Representative IHC staining for Plexin-B2 in a GBM (FIG. 3Fi), an oligodendroglioma (FIG. 3Fii), and normal brain (Fiii). (FIGS. 3Gi-iv) Representative IHC staining for fibulin-1 in a GBM (Gi), an LGA (Gii, an example of low expression), an oligodendroglioma (Giii, an example of high expression), and normal brain (Giv). (FIGS. 3Hi-iv) Representative IHC staining for LINGO in a GBM (Hi), 2 oligodendrogliomas (Hii, an example of low expression; and Hiii, an example of high expression), and normal brain (Hiv). White arrow heads depict regions that highly stain for each biomarker. Magnification of all panels is 40×.

(FIG. 5A) Fibulin-1 (FBLN1), (FIG. 5B) SLIT3, (FIG. 5C) Lingo1, (FIG. 5D) Spondin1 (SPON1), (FIG. 5E) Plexin-B2 (PLXNB2) expression for mesenchymal (Mes) or proneural (PN) GBM subtypes obtained from TCGA (either (i) Affymetrix or (ii) Agilent), (iii) Rembrandt, or (iv) Erasmus databases. Increased Fibulin1 (FIG. 5A), SLIT3 (FIG. 5B), and Plexin-B2 (FIG. 5E) expressions are associated with mesenchymal phenotype in GBM (compared with the proneural subtype), whereas increased Lingo1 (FIG. 5C) and Spondin1 (FIG. 5D) expressions are associated with the proneural subtype. P-values for each marker are shown for each database. For statistical analysis, a Welch's two-sample t-test was used.

(FIG. 9A) Gaussian fit of a representative GL261 tumor volume growth curve. Red Dashed line indicates 95% confidence level, green dashed line indicates 99% confidence level. Modeling was done using a Mathematica-based program (Mathematica 7.0, Wolfram). A typical β value is shown on the curve. (FIG. 9B) Average β Values of Gaussian Curves as a function of Treatment. Significant differences (*p=0.025) were found only between the ELTD1 treatment group and the untreated group, or the Avastin treatment group compared to the ELTD1 treatment group.

(FIG. 10A) Animal survival curves for GL261 glioma-bearing mice either untreated (UT) (n=5), or treated with antibodies against either ELTD1 (ELTD) (n=5), c-Met (n=5), VEGF (n=4) or VEGF2 (alternative antibody against VEGF) (n=4). There was a significant increase in survival for all treated groups (p<0.05 for ELTD, p<0.01 for c-Met, VEGF or VEGF2), compared to untreated mice. (FIG. 10B) Representative tumor growth (measured as tumor volumes (mm3)) curves for GL261 glioma-bearing mice that were either untreated (UT) (closed black diamonds) or treated with antibodies against either ELTD1 (open white squares), VEGF (closed black triangles) or c-Met (grey circles). Exponential growth curves (UT: dash-dot-dot line; ELTD!: solid line; VEGF: dashed line; and c-Met: dotted line) were modeled from the raw data of individual data points for each treatment group.

(FIGS. 11A-D) Representative T2-weighted MR images from GL261 glioma-bearing mice (21 days following intracerebral implantation of GL261 cells) that were either untreated (FIG. 11A), or treated with antibodies against VEGF (FIG. 11B), ELTD1 (FIG. 11C) or c-Met (FIG. 11D). Tumor boundaries are lightly outlined. (FIG. 11E) Histogram depicting tumor volumes (mm³), as measured from multiple MR image slices for either GL261 glioma mice that were untreated (UT) or treated with antibodies against VEGF, VEGF2 (another anti-VEGF antibody), ELTD1 (ELTD) or c-Met. There was a significant decrease in tumor volumes for all treated groups (p<0.01 for VEGF, p<0.05 for VEGF2, p<0.001 for ELTD, and p<0.01 for c-Met) compared to UT animals.

(FIG. 12A-D) Representative histology slides (H&E) obtained from GL261 glioma-bearing mice that were either untreated (UT) (A), or treated with anti-ELTD1 (B), anti-c-Met (C), or mouse anti-VEGF (D) antibodies. Example of mitosis is depicted in panel A with an arrow (black). Panel insert in A indicates atypical mitosis. (E) Histogram of mitotic index for all treatment groups (UT (n=5, black bar), or anti-ELTD1 (n=4; white bar), anti-c-Met (n=4; dark gray bar) or anti-VEGF (n=4; light gray bar) antibody therapies). Significant decreases in the mitotic index were found for anti-ELTD1 and anti-c-Met treatment groups compared to untreated mice ($p<0.05$ for both).

(FIGS. 13A-D) Representative IHC slides for CD-31 obtained from GL261 glioma-bearing mice that were either untreated (UT) (FIG. 13A), or treated with anti-ELTD1 (FIG. 13B), anti-c-Met (FIG. 13C), or mouse anti-VEGF (FIG. 13D) antibodies. (FIG. 13E) Histogram of MVD for all treatment groups (UT (n=11, black bar), or anti-ELTD1 (n=6; white bar), anti-c-Met (n=12; dark gray bar) or anti-VEGF (n=9; light gray bar) antibody therapies). Significant decreases in MVD were found for only the anti-ELTD1 treatment group compared to untreated mice ($p<0.01$). Anti-ELTD1 therapy also had a significantly decreased MVD compared to anti-c-Met ($p<0.01$) or anti-VEGF ($p<0.05$) therapies.

(FIGS. 14A-B) Representative T2-weighted MR images from either untreated (UT) (FIG. 14A) or ELTD1 (ELTD) antibody treated (FIG. 14B) GL261 glioma bearing mice. (FIG. 14C-D) Representative MR angiograms overlaid on top of T2-weighted MR images from either UT (FIG. 14C) or ELTD antibody treated (FIG. 14D) GL261 glioma bearing mice. (FIG. 14E) Histogram of tumor blood volumes (mm3) measured from MR angiograms obtained from GL261 glioma-bearing mice from either UT or mice treated with antibodies against ELTD or VEGF. There was a significant decrease in tumor blood volumes for the ELTD-treated mice ($p<0.0001$) compared to UT animals.

(FIGS. 15A-B) Representative T2-weighted MR images from either untreated (UT) (FIG. 15A) or ELTD1 (ELTD) antibody treated (FIG. 15B) GL261 glioma bearing mice. (FIG. 15C-D) Representative MR perfusion maps from either UT (FIG. 15C) or ELTD antibody treated (FIG. 15D) GL261 glioma bearing mice. (FIG. 15E) Histogram of normalized (against muscle tissue) tumor rCBF (relative cerebral blood flow) differences at late to early time periods for tumor growth measured from MR perfusion images obtained from GL261 glioma-bearing mice from either UT or mice treated with antibodies against ELTD or VEGF. There was a significant decrease in tumor blood volumes for the ELTD-treated mice ($p<0.0001$) or VEGF-treated mice ($p<0.001$), compared to UT animals.

FIG. 16. Anti-Plexin-B2 antibody therapy increases animal survival in a GL261 mouse glioma model. Animal survival curves for GL261 glioma-bearing mice either untreated (UT) (n=5), or treated with an antibody against Plexin-B2 (n=5). There was a significant increase in survival for the treated group ($p<0.05$), compared to untreated mice.

FIGS. 17A-C. Anti-Plexin-B2 antibody treatment decreases tumor volumes in a mouse GL261 glioma model. (FIG. 17A) Histogram depicting tumor volumes (mm3), as measured from multiple MR image slices for either GL261 glioma mice that were untreated (UT) or treated with an antibody against Plexin-B2. There was a significant decrease in tumor volumes for the treated group ($p<0.05$) compared to UT animals. (FIGS. 17B-C) Representative T2-weighted MR images from GL261 glioma-bearing mice (21 days following intracerebral implantation of GL261 cells) that were either treated with an antibody against Plexin-B2 (FIG. 17B) or untreated (FIG. 17C). Tumor boundaries are outlined.

FIG. 18. Anti-Spondin-1 antibody therapy increases animal survival in a GL261 mouse glioma model. Animal survival curves for GL261 glioma-bearing mice either untreated (UT) (n=5), or treated with an antibody against Spondin-1 (n=5). There was a significant increase in survival for the treated group ($p<0.05$), compared to untreated mice.

FIGS. 19A-C. Anti-Spondin-1 antibody treatment decreases tumor volumes in a mouse GL261 glioma model. (FIG. 19A) Histogram depicting tumor volumes (mm3), as measured from multiple MR image slices for either GL261 glioma mice that were untreated (UT) or treated with an antibody against Spondin-1. There was a significant decrease in tumor volumes for the treated group ($p<0.05$) compared to UT animals. (FIGS. 19B-C) Representative T2-weighted MR images from GL261 glioma-bearing mice (21 days following intracerebral implantation of GL261 cells) that were either treated with an antibody against Spondin-1 (FIG. 19B) or untreated (FIG. 19C). Tumor boundaries are outlined.

DESCRIPTION OF ILLUSTRATIVE EMBODIMENTS

Figure 4:
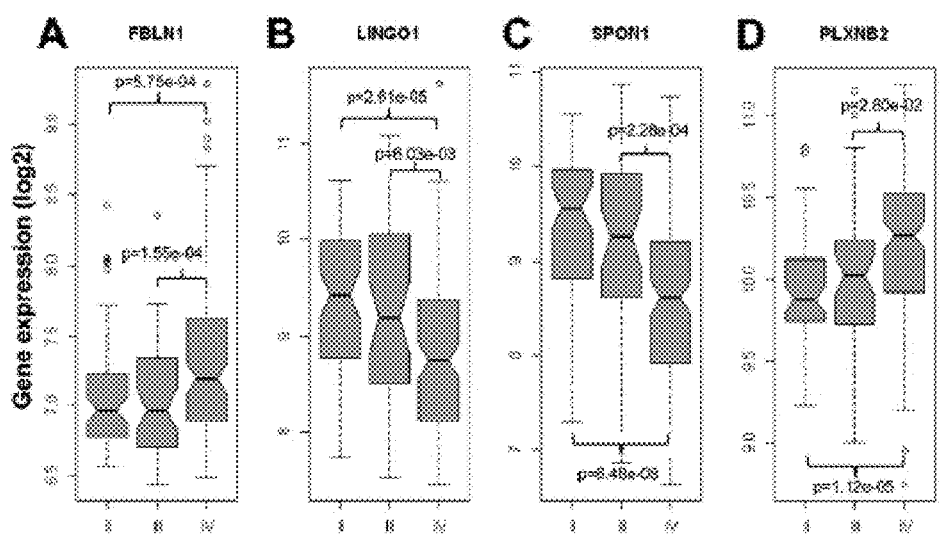
FIG. 4A-D: Increased expression of Fibulin-1, Lingo1, Spondin1, or Plexin-B2 biomarkers is associated with higher grade in gliomas in the Rembrandt gene expression database. Fibulin-1 and Plexin-B2 expressions were found to be significantly higher in grade IV gliomas, and conversely Lingo1 and Spondin1 expressions were significantly lower compared with grade II and grade III gliomas data sets. Significant differences between Grades II and III or Grades II and IV are shown for each marker. For statistical analysis, a Welch's two-sample t-test was used.
Figure 5:
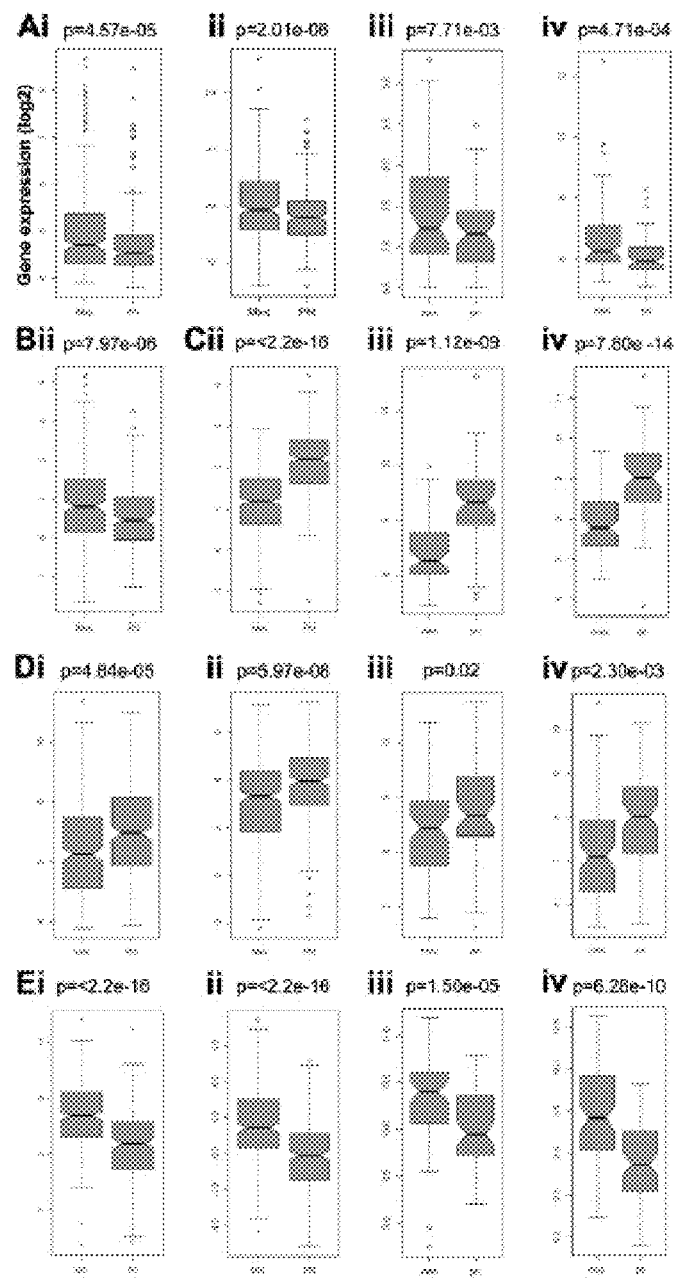
FIGS. 5Ai-Eiv: Biomarker gene expressions in GBM subtypes.

The inventors have demonstrated that antibodies against ELTD1 can slow the growth of gliomas in vivo, thereby validating ELTD1 as a therapeutic target in this type of cancer. In addition, several other protein-Fibulin-1 (FBLN1), SLIT3, LING1, Spondin1 (SPON1), and Plexin-B2 (PLXNB2) have been validated as biomarkers for glioma. These and other aspects of the disclosure are described in greater detail below.

I. Gliomas

Gliomas are a diverse group of brain tumors that arise from the normal "glial" cells of the brain. The most important determinant of survival for gliomas is the "grade" of the glioma. The low-grade gliomas have a protracted natural history, while the high grade gliomas (anaplastic astrocytoma and glioblastoma multiforme) are much more difficult to successfully treat. The gliomas have specific signs and symptoms that are primarily related to the location of the glioma.

The temporal lobe gliomas, for example, may cause epilepsy, difficulty with speech or loss of memory. The frontal lobe gliomas may cause behavioral changes, weakness of the arms or legs or difficulty with speech. The occipital gliomas may cause loss of vision. The parietal gliomas may cause loss of spatial orientation, diminished sensation on the opposite side of the body, or inability to recognize once familiar objects or persons.

Grading according to degree of malignancy was first proposed in 1949. In this classification, astrocytomas and glioblastomas represent different grades of malignancy of the same tumor. Grade I tumors, typically slow growing, are characterized by most cells having normal characteristics, and few mitotic features. Endothelial proliferation is absent. Grade II tumors, previously designated "astroblastomas," are characterized by an increased number of cells with polymorphic nuclei in mitoses. There is no clear line of demarcation from normal tissue. Grade III tumors represent anaplastic astrocytomas and Grade IV tumors represent the typical glioblastoma multiforme, characterized by cellular pleomorphism, vascular proliferation, mitoses, and multinucleated giant cells.

Surgery. The role of surgical resection in the treatment of malignant gliomas remains controversial even after 75 years of experience with primary malignant gliomas. Surgery permits a pathologic diagnosis to be established while the patient is still alive. However, many physicians argue that current radiologic imaging methods, including computed tomography (CT) and magnetic resonance imaging (MRI), permit a malignant brain tumor to be diagnosed without the necessity for attempted tumor resection and, thus, avoid the risks of surgery.

There is evidence that surgical reduction of tumor to very small residual amounts can prolong survival and permit patients to return to active lives. However, retrospective studies are subject to the criticism that the extent of attempted resection depends on the condition of the patient at the time of surgery (age, tumor location, clinical state), and that favorable conditions usually lead the surgeon to attempt a greater resection. Therefore, in such studies, it is not clear that the extent of surgery is as important to survival as are the more favorable prognostic variables. Nevertheless, these results support the surgical removal of the largest possible tumor volume that can be done safely. Patients are frequently able to return to a full, active life without the need for large doses of corticosteroids to ameliorate incapacitating symptoms.

Radiation. The proper portals and doses of radiation for brain tumors have changed with the advent of better imaging techniques. It has been reported in controlled studies that postoperative whole-brain radiation therapy increases patient survival over surgery alone. Other data showed that patients receiving 5,500 to 6,000 cGy of radiation live significantly longer than those receiving 5,000 cGy.

Prolonged survival has been reported in patients with recurrent malignant gliomas who were treated with temporarily implanted $I^{125}$ sources. A phase III trial randomized newly diagnosed patients to receive either (a) postoperative temporary $I^{125}$ seed implantation in the residual tumor bed, followed by standard external-beam radiotherapy plus IV BCNU; or (b) external radiotherapy plus BCNU, without seed implantation. Preliminary review of the results demonstrated that patients who received $I^{125}$ seeds lived longer than those who did not receive seeds, although the difference did not quite reach statistical significance. The study suggests but does not prove that brachytherapy extends survival beyond that achievable with external radiotherapy alone.

Radiosurgery. Radiosurgery, either by gamma knife or linear accelerator, has been shown to be effective in the treatment of arteriovenous malformations, small primary and metastatic brain tumors, and benign brain tumors, such as meningiomas and acoustic neuromas. Its investigational use in the treatment of gliomas has been addressed in several reports. In one trial, 37 patients received radiosurgery (1,000 to 2,000 cGy) to residual contrast-enhancing tumor after treatment with conventional external-beam radiation therapy. Local recurrence still occurred, but overall survival time may have been prolonged. Of the 37 patients, 7 (19%) required reoperation at a median time of 5 months after radiosurgery to remove necrotic tumor.

A major problem with radiosurgery (as with brachytherapy) is bias in the selection of patients for treatment. However, radiosurgery may be of benefit in a small group of good-prognosis patients with small tumors.

Chemotherapy. In 1983, it was reported that surgery plus radiation therapy and BCNU chemotherapy significantly adds to the survival of patients with malignant glioma, as compared with surgery plus radiation therapy without chemotherapy. High-dose methylprednisolone does not prolong survival. Both procarbazine and streptozotocin have demonstrated effectiveness similar to that of BCNU. BCNU alone is as effective as BCNU followed by procarbazine, or BCNU plus hydroxyurea followed by procarbazine plus teniposide. Methotrexate also has been reported to be effective in treating gliomas.

Intra-arterial BCNU is no more effective than intravenous BCNU and substantially more toxic. Serious toxicity induced by intra-arterial BCNU included irreversible encephalopathy and/or visual loss ipsilateral to the infused carotid artery. In the same study, fluorouracil did not influence survival. Neuropathologically, intra-arterial BCNU produced white matter necrosis. Intra-arterial cisplatinum is safer than BCNU administered by the same route but is no more effective than another nitrosourea, PCNU.

Over the past several years, there has been increasing interest in the use of targeted interstitial drug delivery using biodegradable microspheres and wafers. In a multicenter controlled trial, 222 patients with recurrent malignant gliomas who required reoperation were randomly assigned to receive surgically implanted biodegradable polymer discs containing 3.85% of BCNU or discs containing placebo. Median survival of the 110 patients who received BCNU polymers was significantly longer than that of the 112 patients who received placebo polymers (31 versus 23 weeks).

In addition to these controlled survival-based clinical trials, a large number of agents have also been tested in response-based studies in glioma patients. To date, however, no drug has been found to be more effective than the nitrosoureas. The combination of procarbazine, CCNU, and vincristine (PCV) has become a popular chemotherapeutic regimen for malignant glioma, and may be more effective than BCNU alone.

A. Glioblastoma Multiforme

Glioma-glioblastoma multiforme (GBM), referred to a Grade IV glioma, is the most malignant of the neuroepithelial neoplasms, characterized by cellular pleomorphism, numerous mitotic figures, and often multinucleated giant cell. Proliferation of the vascular endothelium is seen as well as areas of necrosis with circumjacent pseudopalisading of the neoplastic cells. It can appear as either a well-circumscribed globular mass or a more diffuse mass lesion. The cut surface reveals necrosis, fatty degeneration, and hemorrhage. Hemorrhages have been found in 40%, with necrosis in up to 52% of the cases. The tumor is usually solid, although cysts may be present. Rarely the tumor consists of a solitary cyst and mural nodule.

Glioblastoma multiforme constitutes approximately 7% of childhood intracranial neoplasms. The overall male to female ratio in children is 3:2. In adults, glioblastomas are noted most frequently in the frontal lobe with the temporal lobe second in frequency. Childhood glioblastomas of the cerebral hemispheres are also located most often in the frontal lobe; with the second most frequent site being the parietal lobe. Primary glioblastoma of the spinal cord in childhood is rare.

Glioblastoma multiforme in children appears to have two characteristic courses, each of which is related to the location of the tumor. Glioblastomas of the brainstem, a more primitive part of the central nervous system, occur at a younger age and have a shorter mean survival relative to those of the cerebral hemispheres. Glioblastoma multiforme of the cerebral hemisphere, a more highly developed part of the central nervous system, is characterized by onset in older children (13 years) and by a longer mean survival.

Headache is the most common complaint and papilledema the most common physical finding in children with hemispheric glioblastoma. Seizures are noted in up to one third of the children. Survival rates in patients with glioblastoma multiforme is uniformly poor. In studies of children treated with surgery and intracranial radiation, only one third of the children are alive one year after diagnosis. Survival of children with glioblastoma multiforme of either of the cerebral hemispheres or the brainstem has significantly increased since the advent of dexamethasone therapy. Presently therapy consists of surgery plus combination chemotherapy.

In summary it can be said that glioblastoma multiforme behaves similarly in both children and adults. The course of intracranial glioblastomas in children is more rapidly fatal than that of other similarly situated gliomas in childhood. While the overall survival rate is very poor in patients with a glioblastoma multiforme, intensive chemotherapy with surgical resection does offer some hope in increasing survival time among children.

B. Astrocytoma

Astrocytomas are tumors that arise from brain cells called astrocytes. Gliomas originate from glial cells, most often astrocytes. Sometimes the terms "astrocytoma" and "glioma" are used interchangeably. Astrocytomas are of two main types—high-grade and low-grade. High-grade tumors grow rapidly and can easily spread through the brain. Low-grade astrocytomas are usually localized and grow slowly over a long period of time. High-grade tumors are much more aggressive and require very intense therapy. The majority of astrocytic tumors in children are low-grade, whereas the majority in adults are high-grade. These tumors can occur anywhere in the brain and spinal cord. Common sites in children are the cerebellum (the area just above the back of the neck), cerebral hemispheres (the top part of the brain), and the thalamus or hypothalamus (located in the center of the brain).

Astrocytomas account for the majority of pediatric brain tumors. About 700 children are diagnosed with low-grade astrocytomas each year. In children, about 90 percent of astrocytomas are low-grade; only about 10 percent are high-grade.

Clinical features and symptoms depend on the location of the tumor and the child's age. The most common location is the cerebellum. Patients with cerebellar tumors have symptoms that include headache, vomiting and unsteadiness in walking. Tumors in the cerebral hemispheres commonly present with seizures: occasionally there is weakness of the arms and legs. Tumors in the hypothalamus often present with visual problems, while thalamic tumors cause headaches and arm or leg weakness.

Complete surgical removal of the tumor (resection) is the best option for tumors in areas where this can be done without damaging the normal, surrounding brain. For low-grade astrocytomas that are completely removed, further therapy is usually not needed. If the surgeon cannot completely remove the tumor, chemotherapy or radiation therapy may be given. The choice of treatments depends on the age of the patient, tumor location; some patients may even be followed without treatment. Radiation therapy is used for older children and those whose tumors keep growing despite chemotherapy. About 90 percent of children with low-grade astrocytomas are alive five years from diagnosis.

High-grade astrocytomas can rarely be removed totally because they often affect large areas of the brain by the time symptoms are obvious. All patients with high-grade astrocytomas usually receive chemotherapy regardless of age. Most, except the very youngest, also receive radiation therapy. Currently, the prognosis is poor in the group of patients. The subset of patients who have high-grade tumors that can be removed may have survival rates of 35 to 40 percent after postsurgical irradiation with chemotherapy. The survival of other patients is very poor.

Research efforts for the low-grade astrocytomas focus on developing chemotherapy regimens that control tumor growth with fewer side effects on other organs of the body. Because these tumors grow slowly, the strategy is to give less intensive chemotherapy over longer periods of time. For older children and those whose tumors progress despite chemotherapy, new radiation techniques are under study to deliver more localized therapy with minimal effects on the normal brain.

For high-grade tumors, new approaches include use of new chemotherapy drugs, and the potential option of high doses of chemotherapy. Investigational new approaches, including new chemotherapy drugs and gene therapy to help protect the bone marrow from the side effects so that more intensive chemotherapy can be given are in various stages of development.

C. Oligodendroglioma and Anaplastic Oliogodendroglioma

Oligodendrogliomas are believed to be tumors of cells called oligodendrocytes that have a role in the structure and function of the brain. However, the origin of these tumor cells has been questioned. Oligodendrogliomas are classified as low grade oligodendroglioma (less aggressive) and anaplastic oligodendroglioma (more aggressive). More common that pure oligodendrogliomas are low grade and anaplastic tumors that are a mixture of astrocytoma and oligodendroglioma ("oligoastrocytomas").

The initial treatment of low grade oligodendroglioma and oligoastrocytoma consists of maximal surgery. The role of radiation therapy has been disputed, but younger people with minimal residual disease after surgery may have radiation therapy deferred as long as there is adequate monitoring of the tumor by MRI or CT scanning.

Anaplastic oligodendrogliomas and mixed oligoastrocytomas are more sensitive to chemotherapy than astrocytomas. A high rate of response to the use of PCV (procarbazine, CCNU, vincristine) chemotherapy has made the use of chemotherapy prior to radiation therapy the standard of care for these tumors. The actual effectiveness of this treatment regimen is currently being investigated in a large multinational trial.

Additionally, low grade oligodendrogliomas are also sensitive to chemotherapy, and PCV can be used when low grade tumors begin to grow despite prior radiation therapy.

II. Glioma Biomarkers

A. ELTD1

ELTD1 is not well characterized. Based upon its sequence, ELTD1 is a member of the secretin family of G-protein-coupled peptide hormone receptors and belongs to the epidermal growth factor-seven-transmembrane (EGF-TM7) subfamiliy (Nechiporuk et al., 2001). Structurally, it contains a large extracellular domain with EGF-like repeats, a seven-transmembrane domain, and a short cytoplasmic tail (Nechiporuk et al., 2001). ELTD1 was first identified to be developmentally regulated in rat fetal and postnatal cardiomyocytes (Nechiporuk et al., 2001). ELTD1 has also been identified with its ligand dermatan sulfate in rheumatoid synovial tissue within rheumatoid arthritis patients. In more obscure roles, variations in ELTD1 have been associated as a risk factor for cannabis use disorders (Agrawal et al., 2008.; Agrawal and Lynskey, 2009), tick burden in cattle (Porto Neto et al., 2011), and subcutaneous fat thickness (Lee et al., 2011). Of more importance to cancer, ELTD1 has been associated as an endothelial marker in microvasculature (Wallgard et al., 2008). The goal in this study was to determine whether or not ELTD1 could be used as a marker for glioma-related processes, and use IHC and molecular magnetic resonance imaging (MRI) to validate its presence in human and rodent gliomas.

The inventors previously identified ELTD1 as a glioma-associated marker via a bioinformatic method, and experimentally validated its presence in both rodent and human gliomas via IHC and molecular MRI analyses in a F98 rodent glioma model (Towner et al., 2013). For IHC, ELTD1 was compared to traditional IHC markers for human gliomas including VEGF (vascular endothelial growth factor), GLUT-1 (glucose transporter 1), CAIX (carbonic anhydrase IX), and HIF-1α (hypoxia inducible factor-1α). ELTD1 expression in human gliomas was also evaluated from gene expression databases (Rembrandt, Erasmus, and TCGA) to establish if this biomarker is differentially expressed in varying glioma grades. The results demonstrated that the differential presence of ELTD1 in gliomas, as compared to non-diseased regions, can proved diagnostic either alone or in combination with other glioma-specific biomarkers, as it is detected in both human GBM and rodent models for gliomas.

The accession numbers for ELTD1 protein and mRNA are Q9HBW9 and NM_022159, respectively.

B. Spondin 1

Spondin-1 (also known as F-spondin) is a protein that in humans is encoded by the SPON1 gene. It is secreted by cells of the floor plate and may be involved in axon guidance. The protein contains 807 amino acids and is structurally composed of six thrombospondin domains, one reelin domain, and one spondin domain.

The accession numbers for Spondin-1 protein and mRNA are Q9HCB6 and NM_006108, respectively.

C. Plexin-B2

Plexin-B2 is a protein that in humans is encoded by the PLXNB2 gene. Members of the B class of plexins, such as PLXNB2 are transmembrane receptors that participate in axon guidance and cell migration in response to semaphorins.

The accession numbers for Plexin-B2 protein and mRNA are O15031 and NM_012401, respectively.

D. SLIT3

Slit homolog 3 protein is a protein that in humans is encoded by the SLIT3 gene. The protein encoded by this gene is secreted, likely interacting with roundabout homolog receptors to effect cell migration. Two transcript variants encoding different isoforms have been found for this gene.

The accession numbers for SLIT3 protein and mRNA are O75094 and NM_001271946 (variant 1), respectively.

E. Fibulin-1

FBLN1 is the gene encoding fibulin-1, an extracellular matrix and plasma protein. Fibulin-1 is a secreted glycoprotein that is found in association with extracellular matrix structures including fibronectin-containing fibers, elastin-containing fibers and basement membranes. Fibulin-1 binds to a number of extracellular matrix constituents including fibronectin, nidogen-1, and the proteoglycan versican. Fibulin-1 is also a blood protein capable of binding to fibrinogen. FBLN1 has also been shown to interact with entactin, NOV/CCN3, and amyloid precursor protein.

Fibulin-1 has modular domain structure and includes a series of nine epidermal growth factor-like modules followed by a fibulin-type module, a module found in all members of the fibulin gene family. The human fibulin-1 gene, FBLN1, encodes four splice variants designated fibulin-1A, B, C and D, which differ in their carboxy terminal regions. In mouse, chicken and the nematode, *C. elegans*, only two fibulin-1 variants are produced, fibulin-1C and fibulin-1D.

The accession numbers for FBLN1 protein and mRNA are AAH22497 and NM_006487 (variant A), respectively.

F. LINGO1

Leucine rich repeat and Ig domain containing 1 also known as LINGO-1 is a protein encoded by the LINGO1 gene. LINGO-1 contains an N-terminal leucine-rich repeat (LRR) domain, followed by 9 typical LRR domains, C-terminal LRR domain, an IgC2 domain, a transmembrane domain, and a cytoplasmic tail. LINGO-1 interacts with the Nogo receptor.

LINGO-1 is primarily expressed in neuronal tissue, and most abundantly in cortex. It has been implicated in the inhibition of axon regeneration through a ternary complex formed with NgR1 (ligand-binding subunit) and p75 (signal transducing subunit). The inhibitory action is achieved through RhoA-GTP upregulation in response to the presence of MOG, MAG or Nogo-66 in the central nervous system. LINGO-1 also inhibits oligodendrocyte precursor differentiation and myelination, by a mechanism that also involves activation of RhoA, but which apparently does not require 75 or NgR1.

The accession numbers for LINGO-1 protein and mRNA are AAH68558 and NM_032808, respectively.

III. Producing Monoclonal Antibodies

A. General Methods

Antibodies may be produced by standard methods as are well known in the art (see, e.g., Antibodies: A Laboratory Manual, Cold Spring Harbor Laboratory, 1988; U.S. Pat. No. 4,196,265). The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this disclosure were generated using the SP2/0/mIL-6 cell line, an IL-6 secreting derivative of the SP2/0 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Engineering of Antibody Sequences

In various embodiments, one may choose to engineer sequences of the identified antibodies for a variety of reasons, such as improved expression, improved crossreactivity, diminished off-target binding or abrogation of one or more natural effector functions, such as activation of complement or recruitment of immune cells (e.g., T cells). In particular, IgM antibodies may be converted to IgG antibodies. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full length IgG antibodies can be generated by subcloning heavy and light chain Fv DNAs from the cloning vector into a Lonza pConIgG1 or pConK2 plasmid vector, transfected into 293 Freestyle cells or Lonza CHO cells, and collected and purified from the CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

It may be desirable to "humanize" antibodies produced in non-human hosts in order to attenuate any immune reaction when used in human therapy. Such humanized antibodies may be studied in an in vitro or an in vivo context. Humanized antibodies may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985); also incorporated herein by reference. "Humanized" antibodies can alternatively be produced by CDR or CEA substitution. Jones et al. (1986); Verhoeyen et al. (1988); Beidler et al. (1988); all of which are incorporated herein by reference.

In related embodiments, the antibody is a derivative of the disclosed antibodies, e.g., an antibody comprising the CDR sequences identical to those in the disclosed antibodies (e.g., a chimeric, humanized or CDR-grafted antibody). In yet a further embodiment, the antibody is a fully human recombinant antibody.

The present disclosure also contemplates isotype modification. By modifying the Fc region to have a different isotype, different functionalities can be achieved. For example, changing to IgG$_4$ can reduce immune effector functions associated with other isotypes.

Modified antibodies may be made by any technique known to those of skill in the art, including expression through standard molecular biological techniques, or the chemical synthesis of polypeptides. Methods for recombinant expression are addressed elsewhere in this document.

C. Expression

Nucleic acids according to the present disclosure will encode antibodies, optionally linked to other protein sequences. As used in this application, the term "a nucleic acid encoding an antibody" refers to a nucleic acid molecule that has been isolated free of total cellular nucleic acid.

The DNA segments of the present disclosure include those encoding biologically functional equivalent proteins and peptides of the sequences described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

Within certain embodiments, expression vectors are employed to express an antibody in order to produce and isolate the polypeptide expressed therefrom. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

Suitable methods for nucleic acid delivery for transformation of an organelle, a cell, a tissue or an organism for use with the current disclosure are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

D. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

E. Single Chain/Single Domain Antibodies

A Single Chain Variable Fragment (scFv) is a fusion of the variable regions of the heavy and light chains of immunoglobulins, linked together with a short (usually serine, glycine) linker. This chimeric molecule, also known as a single domain antibody, retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single domain or single chain variable fragments lack the constant Fc region found in complete antibody molecules, and thus, the common binding sites (e.g., protein A/G) used to purify antibodies (single chain antibodies include the Fc region). These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

F. Modified Antibodies

1. CARs

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of cancer-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14 g2a-Zeta, which is a fusion of a scFv derived from hybridoma 14 g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signalling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However the best spacer often has to be determined empirically.

Transmembrane Domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed. For example, chimeric CD28 and OX40 can be used with CD3-Zeta to transmit a proliferative/survival signal, or all three can be used together.

"First-generation" CARs typically had the intracellular domain from the CD3 ξ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

Adoptive transfer of T cells expressing chimeric antigen receptors is a promising anti-cancer therapeutic as CAR-modified T cells can be engineered to target virtually any tumor associated antigen. There is great potential for this approach to improve patient-specific cancer therapy in a profound way. Following the collection of a patient's T cells, the cells are genetically engineered to express CARs specifically directed towards antigens on the patient's tumor cells, then infused back into the patient. Although adoptive transfer of CAR-modified T-cells is a unique and promising cancer therapeutic, there are significant safety concerns. Clinical trials of this therapy have revealed potential toxic effects of these CARs when healthy tissues express the same target antigens as the tumor cells, leading to outcomes similar to graft-versus-host disease (GVHD). A potential solution to this problem is engineering a suicide gene into the modified T cells. In this way, administration of a prodrug designed to activate the suicide gene during GVHD triggers apoptosis in the suicide gene-activated CAR T cells. This method has been used safely and effectively in hematopoietic stem cell transplantation (HSCT). Adoption of suicide gene therapy to the clinical application of CAR-modified T cell adoptive cell transfer has potential to alleviate GVHD while improving overall anti-tumor efficacy.

2. ADCs

Antibody Drug Conjugates or ADCs are a new class of highly potent biopharmaceutical drugs designed as a targeted therapy for the treatment of cancer. ADCs are complex molecules composed of an antibody (a whole mAb or an antibody fragment such as a single-chain variable fragment, or scFv) linked, via a stable chemical linker with labile bonds, to a biological active cytotoxic (anticancer) payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional chemotherapeutic agents, antibody-drug conjugates target and attack the cancer cell so that healthy cells are less severely affected.

In the development ADC-based anti-tumor therapies, an anticancer drug (e.g., a cell toxin or cytotoxin) is coupled to an antibody that specifically targets a certain tumor marker. Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents.

A stable link between the antibody and cytotoxic (anticancer) agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic (anti-cancer) agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the cancer cell where it releases the cytotoxic agent. The difference is that the cytotoxic payload delivered via a cleavable linker can escape from the targeted cell and, in a process called "bystander killing," attack neighboring cancer cells.

Another type of cleavable linker, currently in development, adds an extra molecule between the cytotoxic drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

3. BitES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against cancer cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to a tumor cell via a tumor specific molecule.

Like other bispecific antibodies, and unlike ordinary monoclonal antibodies, BiTEs form a link between T cells and tumor cells. This causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

BiTEs that were in clinical trials as of July 2010 include Blinatumomab (MT103) for the treatment of non-Hodgkin's lymphoma and acute lymphoblastic leukemia, directed towards CD19, a surface molecule expressed on B cells; and MT110 for the treatment of gastrointestinal and lung cancers, directed towards the EpCAM antigen.

Utilizing the same technology, melanoma (with MCSP specific BiTEs) and acute myeloid leukemia (with CD33 specific BiTEs) can be targeted. Research in this area is currently ongoing. Another avenue for novel anti-cancer therapies is re-engineering some of the currently used conventional antibodies like trastuzumab (targeting HER2/neu), cetuximab and panitumumab (both targeting the EGF receptor), using the BiTE approach. BiTEs against CD66e and EphA2 are being developed as well.

III. Pharmaceutical Formulations and Treatment of Cancer

A. Cancers

Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Cancer cells to which the methods of the present disclosure can be applied include generally any cell that expresses or overexpresses a tumor marker. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice. Cancers may also be recurrent, metastatic and/or multi-drug resistant, and the methods of the present disclosure may be particularly applied to such cancers so as to render them resectable, to prolong or re-induce remission, to inhibit angiogenesis, to prevent or limit metastasis, and/or to treat multi-drug resistant cancers. At a cellular level, this may translate into killing cancer cells, inhibiting cancer cell growth, or otherwise reversing or reducing the malignant phenotype of tumor cells.

B. Formulation and Administration

The present disclosure provides pharmaceutical compositions comprising antibodies. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Other suitable pharmaceutical excipients include starch, glucose, lactose, sucrose, saline, dextrose, gelatin, malt, rice, flour, chalk, silica gel, sodium stearate, glycerol monostearate, talc, sodium chloride, dried skim milk, glycerol, propylene glycol, water, ethanol and the like.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The antibodies of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or admininstration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

C. Combination Therapies

In the context of the present disclosure, it also is contemplated that antibodies described herein could be used similarly in conjunction with chemo- or radiotherapeutic intervention, or other treatments. It also may prove effective, in particular, to combine antibodies with other therapies that target different aspects of target function.

To kill cells, inhibit cell growth, inhibit metastasis, inhibit angiogenesis or otherwise reverse or reduce the malignant phenotype of tumor cells, using the methods and compositions of the present disclosure, one would generally contact a "target" cell with an antibody according to the present disclosure and at least one other agent. These compositions would be provided in a combined amount effective to kill or inhibit proliferation of the cell. This process may involve contacting the cells with the antibody according to the present disclosure and the other agent(s) or factor(s) at the same time. This may be achieved by contacting the cell with a single composition or pharmacological formulation that includes both agents, or by contacting the cell with two distinct compositions or formulations, at the same time, wherein one composition includes the antibody according to the present disclosure and the other includes the other agent.

Alternatively, the antibody therapy may precede or follow the other agent treatment by intervals ranging from minutes to weeks. In embodiments where the other agent and the antibody are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either antibody or the other agent will be desired. Various combinations may be employed, where an antibody according to the present disclosure is "A" and the other therapy is "B", as exemplified below:

A/B/A B/A/B B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/B/A/A A/A/B/A

A/B/B/B B/A/B/B B/B/A/B

Other combinations are contemplated. Again, to achieve cell killing, both agents are delivered to a cell in a combined amount effective to kill the cell.

Agents or factors suitable for cancer therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," may be used. This may be achieved by irradiating the localized tumor site; alternatively, the tumor cells may be contacted with the agent by administering to the subject a therapeutically effective amount of a pharmaceutical composition.

Various classes of chemotherapeutic agents are comtemplated for use with the present disclosure. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The disclosure also encompasses the use of a combination of one or more DNA damaging agents, whether radiation-based or actual compounds, such as the use of X-rays with cisplatin or the use of cisplatin with etoposide. The agent may be prepared and used as a combined therapeutic composition.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in cancer therapy in accordance with the present disclosure.

Another possible therapy is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In addition, it also is contemplated that immunotherapy, hormone therapy, toxin therapy and surgery can be used. In particular, one may employ targeted therapies such as Avastin, Erbitux, Gleevec, Herceptin and Rituxan.

One particularly advantageous approach to combination therapy is combine the antibodies of the present disclosure with one or more of an anti-VEGF antibody, an anti-EGFR antibody or an anti-c-Met antibody.

IV. Antibody Conjugates

Antibodies may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., immunosuppression/anti-inflammation. Non-limiting examples of such molecules are set out above. Such molecules are optionally attached via cleavable linkers designed to allow the molecules to be released at or near the target site.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups are often used to bind radioisotopes to antibody and exist as metallic ions are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277, 437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, there are immunodetection methods for binding, purifying, removing, quantifying and otherwise generally detecting tumor markers. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of antibodies also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to antigen present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple sense, are binding assays. Certain preferred immunoassays are the various types of enzyme linked immunosorbent assays (ELISAs) and radioimmunoassays (RIA) known in the art Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the marker is added to the wells. After binding and washing to remove non-specifically bound immune complexes, the bound antigen may be detected. Detection may be achieved by the addition of another antibody that is linked to a detectable label. This type of ELISA is a simple "sandwich ELISA." Detection may also be achieved by the addition of a second anti-marker antibody, followed by the addition of a third antibody that has binding affinity for the second antibody, with the third antibody being linked to a detectable label.

In another exemplary ELISA, the samples suspected of containing the marker antigen are immobilized onto the well surface and then contacted with the antibody. After binding and washing to remove non-specifically bound immune complexes, the bound antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. MRI

Magnetic resonance imaging (MRI), nuclear magnetic resonance imaging (NMRI), or magnetic resonance tomography (MRT) is a medical imaging technique used in radiology to investigate the anatomy and function of the body in both health and disease. MRI scanners use strong magnetic fields and radiowaves to form images of the body. The technique is widely used in hospitals for medical diagnosis, staging of disease and for follow-up without exposure to ionizing radiation.

MRI has a wide range of applications in medical diagnosis and there are estimated to be over 25,000 scanners in use worldwide. MRI is the imaging modality of choice to help in the diagnosis of neurological diseases, including several brain tumors. MRI techniques can be used to assess morpholigical, functional, structural, metabolic and molecular alterations associated with many diseases, including brain tumors such as gliomas. MRI has an impact on diagnosis and treatment in many specialties although the effect on improved health outcomes is uncertain. Since MRI does not use any ionizing radiation its use is recommended in preference to CT when either modality could yield the same information. MRI is in general a safe technique but the number of incidents causing patient harm has risen. Contraindications to MRI include most cochlear implants and cardiac pacemakers, shrapnel and metallic foreign bodies in the orbits, and some ferromagnetic surgical implants. The safety of MRI during the first trimester of pregnancy is uncertain, but it may be preferable to alternative options. The sustained increase in demand within the healthcare industry for MRI has led to concerns about cost effectiveness and overdiagnosis.

To perform a study the patient is positioned within an MRI scanner which forms a strong magnetic field around the area to be imaged. Most medical applications rely on detecting a radio frequency signal emitted by excited hydrogen atoms in the body (present in any tissue containing water molecules) using energy from an oscillating magnetic field applied at the appropriate resonant frequency. The orientation of the image is controlled by varying the main magnetic field using gradient coils. As these coils are rapidly switched on and off they create the characteristic repetitive noises of an MRI scan. The contrast between different tissues is determined by rate at which excited atoms return to the equilibrium state. Exogenous contrast agents, such as labelel antibodies, may be given intravenously, orally or intra-articularly.

MRI requires a magnetic field that is both strong and uniform. The field strength of the magnet is measured in tesla—and while the majority of systems operate at 1.5 T commercial systems are available between 0.2 T-7 T. Most clinical magnets are superconducting which requires liquid helium. The lower field strengths can be achieved with permanent magnets, which are often used in "open" MRI scanners for claustrophobic patients.

E. Immunodetection Kits

In still further embodiments, there are immunodetection kits for use with the immunodetection methods described above. The immunodetection kits will thus comprise, in suitable container means, a first antibody that binds to antigen, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with embodiments discussed herein.

The kits may further comprise a suitably aliquoted composition of the antigen, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody, antigen, and any other reagent containers in close confinement for commercial sale. Such containers may include injection or blow-molded plastic containers into which the desired vials are retained.

V. Examples

The following examples are included to demonstrate preferred embodiments. It should be appreciated by those of skill in the art that the techniques disclosed in the examples which follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Bioinformatic Assessment

A. Materials and Methods

Bioinformatics. By using a bioinformatics method developed in by the inventors (Wren, 2009; Wren, 2004; Giles and Wren, 2008), the inventors conducted a global meta-analysis of approximately 16,000 microarray experiments from the National Center for Biotechnology Information (NCBI) GEO database. For each human gene, the meta-analysis identified a set of 20 genes that were the most consistently and specifically co-expressed with it across the heterogeneous conditions analyzed. Each gene, whether it had any published literature describing its function or not, had its function inferred by analysis of what each of these 20 co-expressed genes had in common. This was done via an automated, large-scale analysis of the peer-reviewed literature (Wren, 2004 and Giles and Wren, 2008) to identify genes that were consistently transcribed with established glioma-related genes, but that have themselves never been associated with gliomas in the literature. This circumvents a problem inherent in the lists of expressed genes derived by microarrays, which identify only those genes that are being actively transcribed at the time of the experiment without detecting proteins that are present but not actively transcribed. That is, GAMMA associates genes frequently cotranscribed regardless of the condition, and then if a statistically significant set of genes has been reported as glioma-associated in the literature, these associations need not be transcriptional to be identified by GAMMA (e.g., they could be from proteomics or genome-wide association studies). The enormous sample size of both microarray data and analyzed abstracts enables us to screen out genes that do not pass a threshold of statistical significance. This associative method works for glioma-derived literature-based associations as well as searches on associated processes (such as angiogenesis, apoptosis, or cell migration), helping corroborate any putative roles in tumorigenesis that the inventors uncover. For each association, the inventors calculate mutual information (a measure of variable dependency) between literature terms to prioritize the strength of association between each protein and a role in gliomas (Wren, 2004). Finally, the inventors obtained increased confidence in the predictions because GAMMA also successfully predicted many established glioma-related genes (e.g., epidermal growth factor receptor, matrix metalloproteinase-2, glial fibrillary acidic protein, fibroblast growth factor 2). These identifications serve as positive controls for predictive capacity.

Immunohistochemistry. The human tissue sample portion of the study was conducted in compliance with the University of Utah Health Sciences Center Institutional Review Board. For IHC analysis, tissue from 50 patients with high-grade gliomas (21 female, 29 male), including 40 GBM, 6 anaplastic astrocytomas, and 4 anaplastic oligodendrogliomas, was compared with tissue from 21 patients (10 female, 11 male) with tumors classified as low-grade gliomas (11 benign oligodendrogliomas, 10 low-grade astrocytomas). Antibodies (Abs) to Spondin1, Plexin-B2, SLIT 3, Fibulin-1, and Lingo1 were available commercially (F-Spondin Ab (S-17), Plexin-B2 Ab (I-16), Slit3 Ab (F-15), and Fibulin-1 Ab (H-190) were all obtained from Santa Cruz Biotechnology, Inc., Santa Cruz, Calif., USA; Lingo1 (LRRN6A)-S596 (C-term) Ab was obtained from Abgent, San Diego, Calif., USA; all human Abs were assessed and found to provide similar results; dilutions were 1:500). A toluidine blue (0.1%) counterstain was used (15 sec). IHC was performed using the Vectastain ABC Kit (Vector Laboratories, Burlingame, Calif., USA). Negative controls were performed by replacing the primary Ab with nonimmune serum. Slides were examined using an Olympus BX41 Microscope. Under 200×(10 ocular×20 objective) magnification, slides were scored by two investigators blinded to the specimen tumor grade or patient information. A score of 0-4 (0=0-25%, 1=25-50%, 2=50-75%, 3=75-100%, 4=100%) was assigned based on the number of cells stained in a given field. In prior papers, the inventors have demonstrated that this method is very reproducible, with good inter-rater reliability (p=0.99, 95% CI (0.99-1.00)) and intra-rater reliability (p=0.96, 95% CI (0.92-0.99)) (20). Each investigator independently reviewed the slide at low power and at random high-power fields when determining the IHC score. Positive expression was considered for scores of 2-4, whereas negative expression was considered for scores of 0 and 1. Percent survival for the GBM, anaplastic astrocytoma, and anaplastic oligodendroglioma patients were 0.0, 0.0 and 50.0%, respectively. Percent survivals for benign oligodendroglioma and low-grade astrocytoma patients were 27.3 and 70.0%, respectively.

Gene Expression Analysis. For the glioblastoma expression microarray analysis, raw Affymetric .cel files and level 3 Agilent expression data were downloaded from the TCGA (The Cancer Genome Atlas; world-wide-web at cancergenome.nih.gov; 529 and 594 GBM samples, respectively), Rembrandt (Repository for Molecular Brain Neoplasia Data; world-wide-web at rembrandt.nci.nih.gov; 229 total astrocytomas, of which 125 are GBM), and Erasmus (NCBI Gene Expression Omnibus; GEO Series GSE16011, world-wide-web at ncbi.nlm.nih.gov/geo/query/acc.cgi?acc=GSE16011; total of 187 astrocytomas, of which 159 are GBM), as well as the corresponding clinical annotations for each. The .cel files were then processed using R and Bioconductor, using a custom computable document format (CDF) file, with background correction, log transformation, and quantile normalization performed using the robust multi-array (RMA) algorithm implemented in R.

For mesenchymal and proneural gene signature definition, the inventors used a composite of signatures from the Phillips et al. (Phillips et al., 2006) and Verhaak et al. (Verhaak et al., 2010). For a given tumor, the metagene mesenchymal and proneural signature score were both calculated. Within a data set, the mesenchymal and proneural metascores were z-score corrected to allow comparison between the two. Tumors were then assigned to one of the signatures based on the higher expressing metagene.

Statistical Analyses. Statistical differences for IHC scoring and expression statistical differences were compared between groups using the Welch two-sample t-test (unpaired, 'two-sided'), with p-values <0.05 considered to be significant.

B. Results

Bioinformatics. Using the GAMMA procedure, the inventros evaluate all genes differentially expressed across 3,651 human two-color microarray experiments as previously described (Wren, 2009) to identify membrane-bound proteins that had not yet been associated with gliomas but whose expression consistently correlates with genes reported to be associated with gliomas. The inventors identified 195 putative candidate markers, all genes predicted or known to be membrane bound and not appearing in any MEDLINE article that mentioned gliomas (or synonymous terms). Of these 195, only 75 had commercial antibodies that the inventors could use to validate with IHC. Fibulin-1, Lingo1 (leucine-rich repeat and Ig domain—containing Nogo receptor interacting protein-1), Spondin1, SLIT3 (Slit homolog), and Plexin-B2 were chosen from among this list of 75 because they all had high scores. With this analysis set to stringent thresholds, the inventors have empirically observed that the FBLN1, LINGO1, SPON1, SLIT3, and PLXNB2 genes were all found to be consistently transcribed with known glioma-associated genes.

GAMMA scores are based on a combination of (1) how many genes out of the 20 top coexpressed analyzed genes showed associations with gliomas based on published reports, and (2) their statistical significance based on random network simulations to estimate the probability that a set of equally frequent terms would associate with gliomas. Only proteins with $p<0.01$ were selected as potential candidates. A flow diagram of the GAMMA approach is illustrated in FIGS. 1A-C.

Immunohistochemistry. Fibulin-1, SLIT3, Lingo1, Spondin1, and Plexin-B2 were all found to be expressed in gliomas in general (FIGS. 2A-B). Fibulin-1 and Lingo were not found to have significantly higher expression ($p>0.05$ for both) when comparing high-grade and low-grade gliomas, whereas all other biomarkers (traditional biomarkers including VEGF, HIF-1α, and GLUT-1 had $p<0.05$, $p<0.05$, and $p<0.01$, respectively), including SLIT3 ($p<0.01$), Spondin1 ($p<0.001$), and Plexin-B2 ($p<0.01$), had significantly higher expression in high-grade compared with low-grade gliomas (FIG. 2A). All five novel biomarkers compared well with VEGF, HIF-1α, or Glut-1, although Lingo1 had a higher average IHC score in both high-grade and low-grade gliomas compared with traditional markers. In low-grade gliomas (low-grade astrocystomas and oligodendromas), Lingo1 had the highest IHC score, followed by Fibulin-1. All of the novel biomarkers were ≥80% positive in high-grade glioma patients, and Fibulin-1, SLIT3, and Lingo1 were >70% positive in low-grade glioma patients (FIG. 2B).

FIGS. 3Ai-Aiii depicts representative IHC staining for VEGF, HIF-1a, GLUT-1, SLIT3, spondin1, Plexin-B2, fibulin-1, and LINGO1 in human high-grade and low-grade gliomas, indicating that high-grade gliomas had substantially higher levels of VEGF, HIF-1a, GLUT-1, SLIT3, spondin1, and Plexin-B2 compared with corresponding low-grade gliomas. In addition to examples depicting low levels in low-grade gliomas (FIG. 3Gii and FIG. 3Hii), both fibulin-1 and LINGO1 had samples with high levels of staining in low-grade gliomas (FIG. 3Giii and FIG. 3Hiii, respectively).

FIG. 4 illustrates that gene expression levels of Fibulin-1, Lingo1, Spondin1, and Plexin-B2 are all significantly different in Grade III or Grade IV gliomas compared with Grade II gliomas. Gene expression data for SLIT3 was found to be poorly represented on the Affymetrix platforms and did not provide conclusive differences in tumor grades in the Agilent TCGA data. Both Fibulin-1 and Plexin-B2 were found to be expressed significantly more in Grade IV gliomas than in Grade II ($p<0.001$ or $p<0.0001$, respectively) or Grade III ($p<0.001$ or $p<0.05$, respectively) gliomas, whereas Lingo1 and Spondin1 were found to have significantly lower expression in Grade IV tumors than in Grade II ($p<0.0001$ for both) or Grade III ($p<0.01$ or $p<0.001$, respectively) tumors.

FIGS. 5A-E shows how each of the biomarkers can be used to differentiate between mesenchymal and proneural GBM subtypes, as measured in four gene expression databases (TCGA (Affymetrix platform), TCGA (Agilent platform), Rembrandt, and Erasmus). Data for SLIT3 were only available in the TCGA (Agilent) database, and Lingo1 data were not available in the TCGA (Affymetrix) database. In three gene databases, Fibulin-1 expression was found to be significantly higher ($p<0.01$) in mesenchymal GBMs, whereas Lingo1 expression was found to be significantly higher ($p<0.0001$) in proneural GBMs. In all four databases, Spondin1 expression was found to be significantly higher ($p<0.05$) in proneural GBMs, whereas Plexin-B2 expression was found to be significantly higher ($p<0.0001$) in mesenchymal GBMs. SLIT3 expression was found to be significantly higher ($p<0.0001$) in mesenchymal GBM compared with proneural GBM.

C. Discussion

The inventors found that each of the algorithmically predicted biomarkers was found in high levels within human gliomas in general, as assessed by IHC, and that some of the biomarkers, such as SLIT3, Spondin1, and Plexin-B2, are expressed at significantly higher in high-grade gliomas than in low-grade gliomas (FIG. 2A) and may be useful diagnostic markers for high-grade gliomas (FIGS. 3A-Hiii). Both Fibulin-1 and Lingo1 were found to be positively expressed in both high-grade and low-grade gliomas with high IHC scores (FIG. 2B), although they did not significantly differentiate between the grades, and these two markers may serve as general glioma markers for all tumor grades. Examples of both high and low levels of these markers are depicted in FIGS. 3A-Hiii. SLIT3, Spondin1, and Plexin-B2 also all fare well in comparison with more traditional IHC markers currently used to diagnose GBM, in that the expression levels of these three biomarkers were similar to those of currently investigated glioma markers including VEGF, HIF-1α, and GLUT-1. HIF-1α has been well documented to be an important diagnostic marker for gliomas, and this marker can be targeted for therapeutic intervention (Flynn et al., 2008; Gillespie et al., 2009; Ragel et al., 2007; Gillespie et al., 2007; Rong et al., 2006; Jensen, 2006; Jensen et al., 2006).

From the gene expression results, the inventors have also demonstrated that there was a strong association with expression of Fibulin-1, Lingo1, Spondon1, and Plexin-B2 in grade IV gliomas compared with either Grade II or Grade III gliomas (FIG. 4). Interestingly, both Fibulin-1 and Plexin-B2 were found to be more highly expressed in Grade IV gliomas, whereas Lingo1 and Spondin1 were found to be less expressed in Grade IV tumors when compared with either Grade II or Grade III gliomas. In addition, when the inventors looked at the GBM tumor subtypes, it looked like there was a significant increase with gene expression of Fibulin-1, Plexin-B2, and SLIT3 for the mesenchymal subtype versus the proneural subtype, which was better associated with increased gene expression of Lingo1 and Spondin1 (FIGS. 5A-E). These findings were found to be consistent in three gene databases for Fibulin-1, Lingo1, Spondin1, and Plexin-B2. Unfortunately, SLIT3 gene data were only useable in the TCGA (Agilent) database. It is reasonable to conclude that Spondin1 and Plexin-B2 expression data in particular are both strong biomarkers of grade (also supported by the IHC data), with Plexin-B2 increased in the mesenchymal subtype and Spondin1 elevated in the proneural subtype.

None of the five proteins had been documented as differentially present on the surface of glioma cells, although SLIT3 was found in a previous study to be hypermethylated in glioma and colorectal cancer cell lines (Dickinson et al., 2004). Spondin1, SLIT3, and Fibulin-1 also had previously reported associations with different cancers. Spondin1 was previously found to be overexpressed in ovarian/peritoneal carcinomas (Davidson et al., 2011; Gyorffy et al., 2008; Kobel et al., 2008) and SLIT3 was widely expressed in human hepatocellular carcinomas (Lin and Chuang, 2012). Fibulin-1 was associated with gastric (Cheng et al., 2008), breast (Pupa, et al., 2004), colon (Wen et al., 2006), and prostate (Wlazlinski et al., 2007) cancers, and its promoter hypermethylation associated with tumor progression in human hepatocellular carcinomas (Kanda et al., 2011). SLIT3 is a predominant ligand transcribed in the early mouse heart and is expressed in the ventral wall of the linear heart tube and subsequently in the chamber (Medioni et al., 2010). The SLIT3 gene at human chromosome 5q34-q35.1 is involved in encoding large secreted proteins functioning as ligands for Roundabout (Robo) receptors, and the SLIT-ROBO signaling pathway is implicated in angiogenesis and endothelial cell migration (Katoh and Katoh, 2005).

Neither Plexin-B2 nor Lingo1 have been previously associated with cancer, although some function is known for these genes. Plexins are a family of genes that are expressed in several organ systems and have been implicated in cell movement and cell-cell interaction (Holl et al., 2012). Plexin-B2 has been reported to be associated with the negative regulation of IL-12/IL-23p40 in dendritic cells (Holl et al., 2012) Plexins are cell surface receptors widely studied in the nervous system, where they mediate migration and morphogenesis through the Rho family of small GTPases (Roney et al., 2011). Plexin-B2 is highly expressed on cells of the innate immune system in the mouse, including macrophages and dendritic cells, and may serve as a negative regulator of basal cell motility (Roney et al., 2011). Although Plexin-B2 has not been associated with cancers, Plexin-B1 has been reported to be involved as a tumor suppressor in melanoma cells (Argast et al., 2009), and plexin-B in general is involved in invasive growth (Conrotto et al., 2004) and angiogenesis (Basile et al., 2004). Lingo1 has been found to be a potent regulator of neural stem cell maturation to neurons, and inhibition of Lingo1 during the first days of neural stem cell differentiation results in decreased neuronal maturation (Zhang et al., 2009; Loov et al., 2012). Lingo1 is a central nervous system transmembrane protein that simultaneously interacts with the Nogo-66 receptor and p75(NTR) or TROY on neurons to form a receptor complex responsible for myelin-mediated neurite outgrowth inhibition (Stein et al., 2012), and thus is a negative regulator of myelination and repair of damaged axons (Pepinsky et al., 2011).

The results presented strongly suggest that the associative analysis method used in this study was able to accurately identify Fibulin-1, Lingo1, Spondin1, Plexin-B2, and SLIT3 as glioma-associated biomarkers. SLIT3, FBLN1, and SPON1 are predicted to influence glioma progression by their role in the extracellular matrix. SLIT3 has established associations with angiogenesis and cell migration, and several genes with known roles in extracellular matrix remodeling (e.g., SPARC and VE-Cadherin) are predicted to be relevant to SLIT3's network. Fibulin-1 has predicted associations with cell motility and invasion, and Spondin1 is specifically predicted to exert its influence via collagen matrix attachments. PLXNB2, however, is predicted to be more relevant to cell proliferation and is predicted to be relevant to the wnt/β-catenin pathway. LINGO1 is probably the most neural-specific protein of the group and, based on the IHC scores, appears to be increasingly important as the tumor grade increases. Each marker has either known or predicted associations to different aspects of glioma tumor growth, and each marker or combination could provide valuable diagnostic information for gliomas.

TABLE 1

GAMMA-associated relationships of potential novel glioma biomarkers (highest GAMMA scores) with cancer growth characteristics and other cancers

| Biomarker | Functional Relationships | Ref. |
|---|---|---|
| SLIT3 | Growth factor, angiogenesis/VEGF, cell proliferation, cell migration, extracellular matrix proteins, epigenetic (hypermethylation) inactivation of SLIT1-3 genes in human cancers, melanoma, breast cancer, ovarian cancer, colorectal cancer, gastric cancer | (Dickinson et al., 2004; Medioni et al., 2010 and Katoh et al., 2005) |
| SPON1 (Spondin1) | Extracellular matrix protein, promotes cell attachment, cell adhesion, angiogenesis/VEGF, cell migration, cell growth; colorectal cancer, ovarian cancer | (Davidson et al., 2011; Gyorffy et al., 2008; Kobel et al., 2008 and Pyle-Chenault et al., 2005) |
| FBLN1 (Fibulin-1) | Extracellular matrix organization (proteins, components), Integrin, basement membrane, TGF-β, growth factor, cell adhesion, cell proliferation, cell growth, cell migration, angiogenesis, matrix metalloproteinases; overexpressed in other cancers, melanoma, breast cancer, hepatocellular carcinoma, prostate cancer | (Cheng et al., 2008; Pupa et al., 2004; Wen et al., 2006; Wlazlinski et al., 2007 and Kanda et al., 2011.) |
| PLXNB2 (Plexin-B2) | Cell proliferation, angiogenesis, cell motility, TGF-β, pro-inflammatory cytokines | (Holl et al., 2012; Roney et al., 2011; Argast et al., 2009; Conrotto et al., 2004; Basile et al., 2004) |
| LINGO1 | Neurogenesis, brain development, EGF receptor binding, astrocytes, glial cells | (Zhang et al., 2009; Loov et al., 2012; Stein et al., 2012 and Pepinsky et al., 2011) |

Example 2

ELTD1

A. Materials

Treatments. Mice (n=4-5 per group) were treated with anti-ELTD1, anti-VEGF, or anti-c-Met antibodies (1 mg/kg in 100 µl saline; every 3 days for up to 21 days). Untreated mice served as controls for statistical comparison.

MRI. MRI experiments were performed on a Bruker Bio-spec 7.0 Tesla/30-cm horizontal-bore magnet imaging system. Animals were immobilized by using 1.5-2.5% isoflurane and 0.8 L/min $O_2$ and placed in a 72-mm quadrature volume coil for signal transmission, and a surface mouse-head coil was used for signal reception. $T_2$-weighted imaging was acquired as previously described by the inventors (Towner et al., 2013). Tumor volumes and tumor blood volumes were calculated from MRI datasets. Percent survival was also determined.

MRA. MR angiography (MRA) was used to obtain macrovascular (tumor blood vessels >50 µm in diameter) images as previously described (Doblas et al., 2010). Briefly, MRA data were acquired within a volume-of-interest of 1.28×1× 0.64 $cm_3$, at an angle of 16° relative to the horizontal plane, and a flip angle of 90°, for a total acquisition time of 25 min (Doblas et al., 2010). Tumor blood volumes were segmented from 3D-MR angiograms and quantified using Mathematica (Towner et al., 2013). Datasets were reconstructed to provide a pixel resolution of 50×78×100 $µm_3$ (Doblas et al., 2010). For analysis, a ROI encompassing blood vessels in the tumor area was selected, and was used to provide absolute tumor blood volumes (Doblas et al., 2010).

Perfusion Imaging. In order to assess microvascular alterations associated with tumor capillaries, the perfusion imaging method, arterial spin labeling (ASL), was used as previously described (Garteiser et al., 2010). Perfusion maps were obtained on a single axial slice of the brain located on the point of the rostro-caudal axis where the tumor had the largest cross-section (Garteiser et al., 2010). The imaging geometry was a 3.5×3.5 $mm_2$ slice, of 1.5 mm in thickness, with a single shot echo-planar encoding over a 64×64 matrix. An echo time of 20 ms and a repetition time of 18 s was used. To obtain perfusion contrast, the flow alternating inversion recovery scheme was used. Briefly, inversion recovery images were acquired using a slice-selective (SS) inversion of the same geometry as the imaging slice or a non-selective (NS) inversion slice concentric with the imaging slice but of 60 mm in thickness. For each type of inversion, 8 images were acquired with inversion times (TI) evenly spaced from 20 ms to 2820 ms. For perfusion data, the recovery curves obtained from each pixel of the non-selective:

$$(S_{NS}(TI)=A-B \cdot e^{-TI/T_1})$$

or selective $$(S_{SS}(TI)=A-B \cdot e^{-TI/T_1}, \text{ with } 1/T_1^*=1/T_1+CBF/\lambda)$$

inversion images were numerically fitted to derive the pixelwise $T_1$ and $T_1^*$ values, respectively (Zhu et al., 2014). The results were stored as maps for further analysis. The longitudinal recovery rates were then used to calculate the cerebral blood flow, CBF (ml/(100 g·min)) on a pixelwise basis using the following relationship:

$$CBF=\lambda \cdot [(1/T_1^*)-(1/T_1)]$$

(Zhu et al., 2014). The partition coefficient, $\lambda$, was scaled by assigning the generally adopted value of 0.9 ml/g (Herscovitch et al., 1985). Regions of interest (ROIs) were manually outlined around the tumor and an appropriate ROI was also taken from the contralateral side of the brain for comparison purposes. To calculate the differences in rCBF values, tumor rCBF values were obtained at late (days 18-26 following intracerebral implantation of cells for untreated mice, and days 20-31 for treated mice) and early (days 10-13 following cell implantation) tumor stages, and normalized to rCBF values in the contralateral brain region of corresponding animals.

Histology and Immunohistochemistry (IHC). All mice were euthanized after the last MRI examination. The whole brain of each animal was removed, preserved in 10% neutral buffered formalin, and processed routinely. Paraffin-embedded tissues were sectioned in 5 µm sections, mounted on frosted glass slides, stained with hematoxylin and eosin (H&E), and examined by light microscopy. A single pathologist evaluated the HE sections of all cases via light microscopy and generated a mitotic index per 5 high-power (400×) fields (HPFs). The region of the tumor sample with the highest overall mitotic activity was chosen for evaluation (field selection method). A single count of 5 HPFs was obtained for each tumor sample. To characterize microvessel density (MVD) and tumor cell invasion, respectively, in both untreated and treated groups, immunohistochemistry for CD-31 (1:25 dilution, rabbit polyclonal, clone ab28364, Abcam, MA) or CD-44 (1:150 dilution, rabbit polyclonal, clone LS-B7732, Lifespan Biosciences, WA) antibodies was performed using an automated immunostainer (Leica, Bond-III, Leica, Buffalo Grove, Ill.). Three region of interest (ROI) with the highest number of blood vessels (200× magnification) were identified in each case. The MVD measurements were captured digitally for each selected ROI and calculated using the Aperio ScanScope Image Analysis System (Aperio, Vista, Calif.) [29]. One ROI with the highest number of positive cells for CD44 was identified in each case at 200× magnification. Expression of CD44s was graded in terms of intensity of staining in each case. Intensity of staining was graded as: negative (0), weak (+1), moderate (+2) or strong (+3) using the Aperio ScanScope Image Analysis System [30]. For all positive cases, localization of staining to the cell membrane, cytoplasm or both was performed.

Statistical Analysis. Statistical analyses was performed by using ANOVA with a post Tukey's multiple comparison test for evaluating differences in tumor volumes between untreated and treated groups. Data was represented as mean±S.D. and P-values <0.05 (*), <0.01 (), <0.001 (*) were considered statistically significant.

B. Results

The inventors recently identified novel glioma-specific biomarkers identified via a GAMMA (global microarray meta-analysis) bioinformatics method, and validated these biomarkers in human gliomas of varying tumor grades. ELTD1 (epidermal growth factor, lactrophilin, and 7 transmembrane domain-containing protein 1 on chromosome 1) was validated as a biomarker in human gliomas, and was determined to be a specific biomarker for high-grade glioblastomas (Towner et al., *Neurosurgery* 72 (1): 77-91, 2013). ELTD1 is an endothelial marker in microvasculature that could be useful in characterizing tumor-associated angiogenesis, both for detecting gliomas in general, and specifically to differentiate high-grade gliomas from low-grade gliomas.

Figure 6:
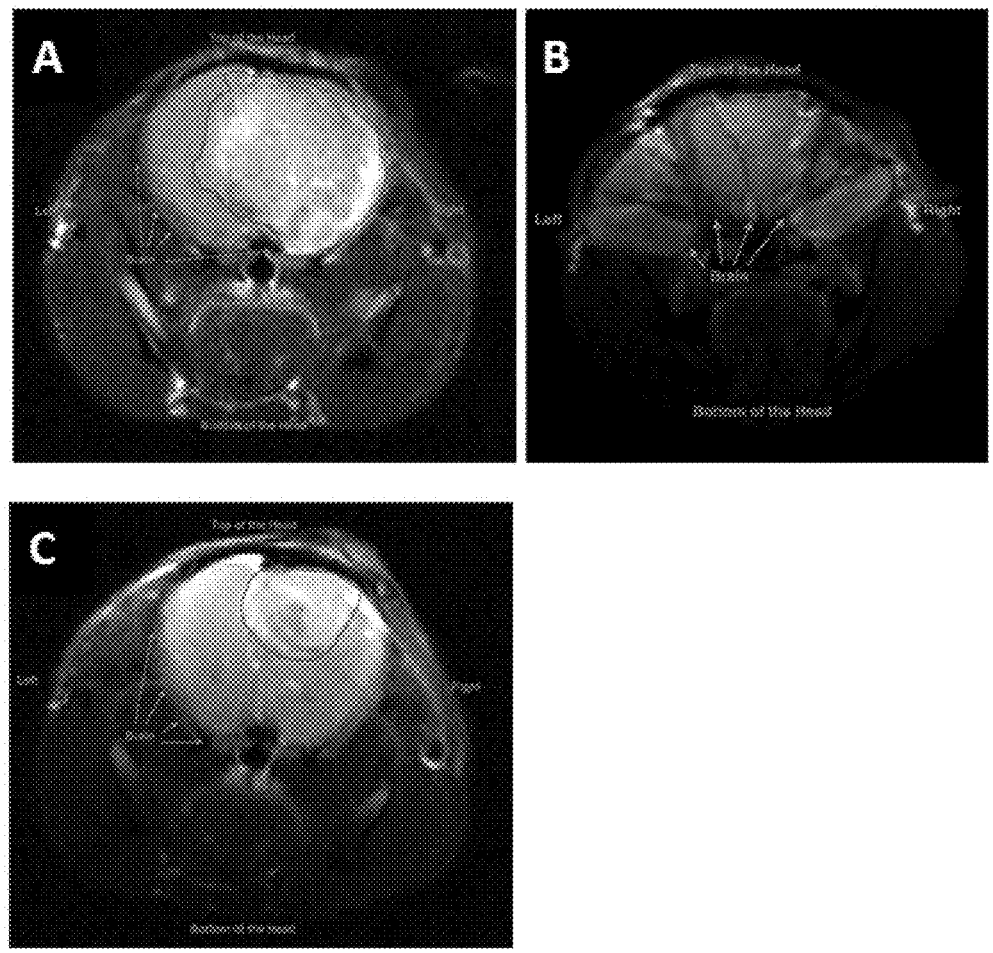
FIGS. 6A-C: In vivo MRI scans of GL261 glioma-bearing mouse brains. Tumors are outlined. Images are of Untreated (FIG. 1A), anti-ELTD1 antibody-treated (FIG. 1B) and Avastin-treated (FIG. 1C) 21 days after GL261 cell implantations.
Figure 7:
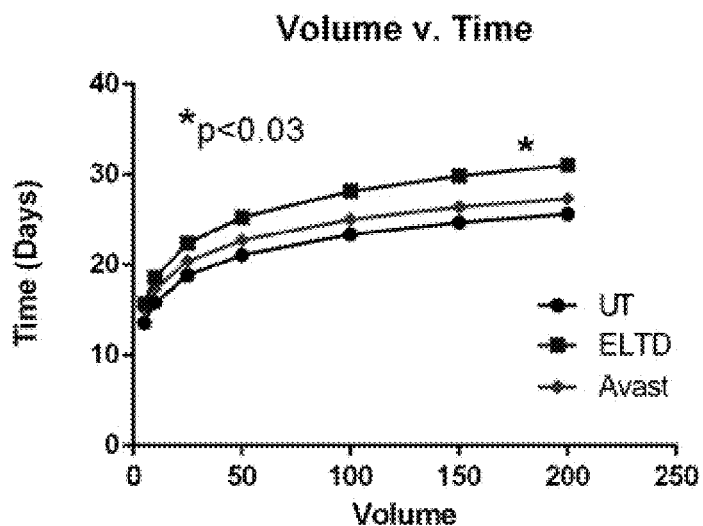
FIG. 7: Average tumor volume (mm³) curves for each treatment group (untreated (UT), ELTD1 (ELTD) or Avast (Avast) as a function of time. Significant differences (*p<0.03) were found between the ELTD1 treatment group and the untreated group.
Figure 8:
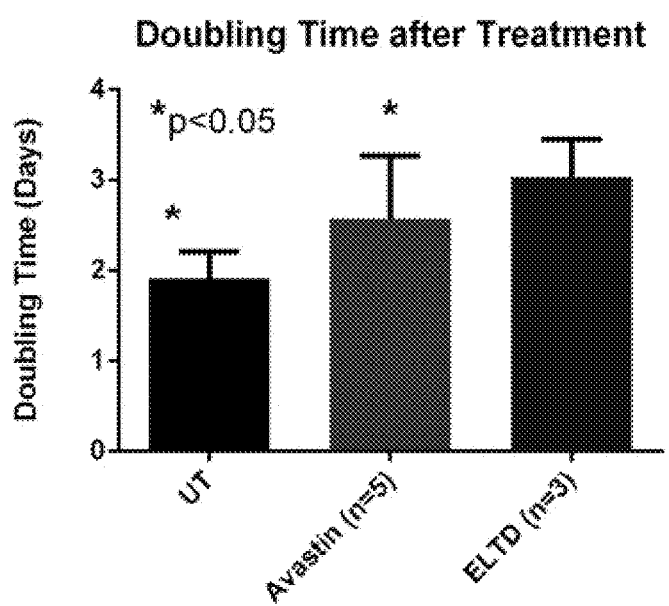
FIG. 8: Doubling time of tumors following treatment. Doubling time is the time that it takes a tumor to double in volume, i.e., the time it would take for a tumor with a volume of 10 mm³ to reach a volume of 20 mm³. There was significance between the untreated group and the ELTD1 treated group or the Avastin group (*p<0.05 for both). Doubling times were calculated using the equation: $V(t) = V_0 * \exp[(\beta/\alpha)(1-(\exp[-\alpha t)])]$ with the first date being the first

Following demonstration of its diagnostic potential, the inventors sought to generate data supporting ELTD1 as an anti-cancer agent in a pre-clinical model (orthotopic GL261 mouse glioma model) for gliomas. FIGS. 6A-C depicts representative examples of GL261 glioma-bearing mice either untreated (FIG. 6A) or treated with either ELTD1 (FIG. 6B), or Avastin (also known as bevacizumab; FIG. 6C). FIG. 7 illustrates the time (days) that it takes for GL261 tumors to reach particular tumor volumes (mm$^3$) ELTD1 took significantly longer to reach a tumor volume of 200 mm$^3$ compared to untreated animals. Tumor doubling times (days) are also shown in FIG. 8, which shows that both ELTD1 or Avastin had significantly higher tumor doubling times compared to untreated tumors. FIGS. 9A-B illustrate the use of a Gaussian fit routine to calculate a β value which is a parameter that can determine treatment response in association with tumor growth. ELTD1-treated tumors were found to have significantly longer β values (days) compared to untreated or Avastin-treated tumors.

These data suggest that an anti-ELTD1 antibody as anti-cancer activity against GL261 gliomas in comparison to untreated tumors or those treated with Avastin (anti-VEGF antibody therapy).

Figure 10:
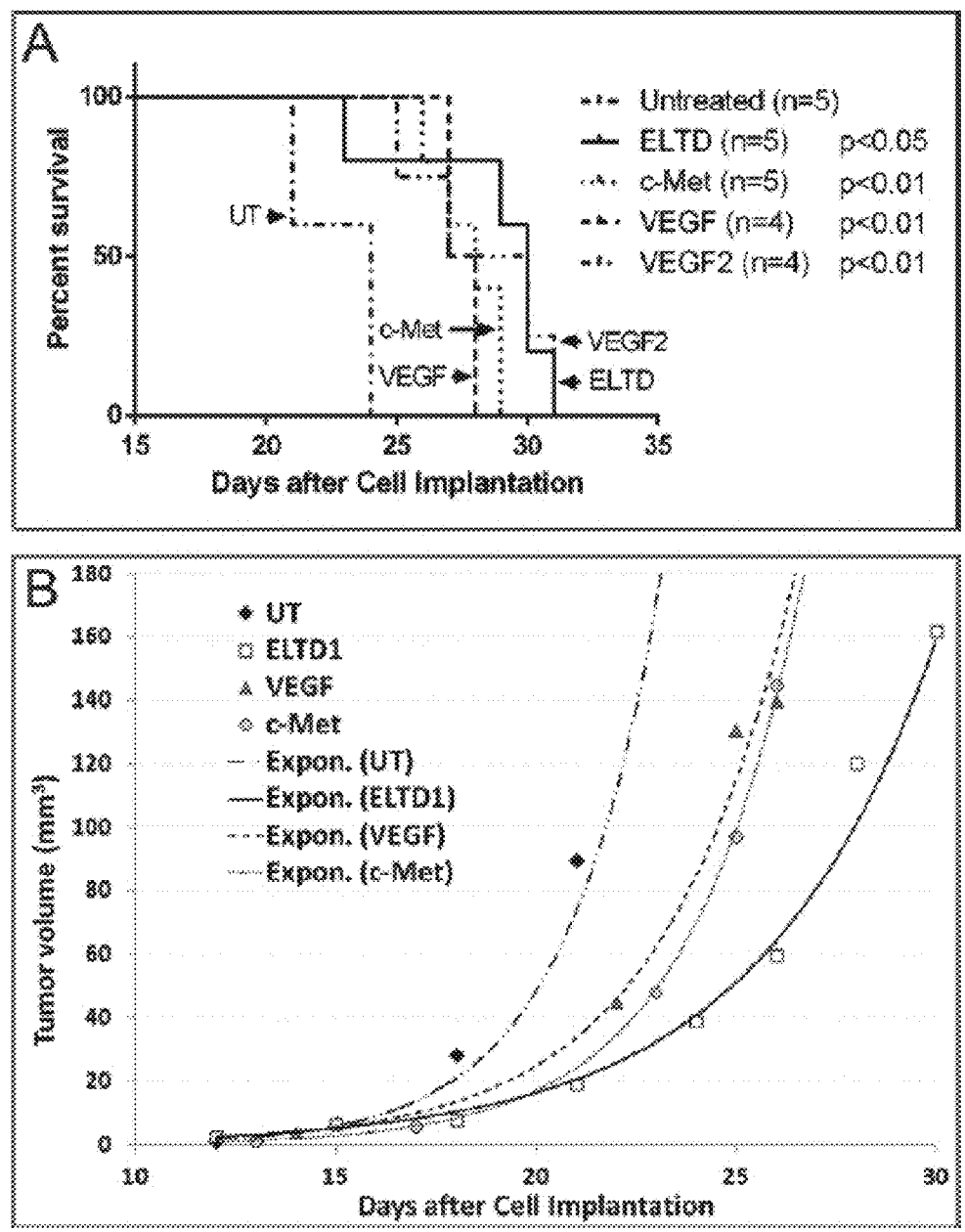
FIGS. 10A-B. Anti-ELTD1 antibody therapy increases animal survival in a GL261 mouse glioma model.

Percent survival of GL261 glioma-bearing mice treated with anti-ELTD1 antibodies was significantly higher (p<0.05) compared to untreated tumors, as depicted in FIG. 10A. Other antibody therapies including anti-mouse anti-VEGF or anti-c-Met antibodies also significantly increased animal survival (p<0.01 for both) when compared to untreated GL261 gliomas (FIG. 10A). FIG. 10B illustrates some representative tumor growth curves (tumor volumes were measured from multiple MRI slices through tumor regions) for the four treatment groups with exponential trendlines. Tumor growth for the untreated group is faster than for either anti-VEGF or anti-c-Met, which are both similar, and anti-ELTD1 has the slowest growth for all groups (FIG. 10B). Representative MR images of GL261 tumor volumes are shown in FIGS. 11A-D. Tumor volumes at 21 days following intracerebral implantation of GL261 cells, were found to be significantly lower in anti-ELTD1 antibody-treated mice (p<0.001) compared to untreated controls (FIG. 11E). Likewise anti-VEGF and anti-c-Met antibody treatments also had significantly decreased tumor volumes (p<0.05 for anti-VEGF, and p<0.01 for anti-c-Met antibody therapies) compared to untreated animals (FIG. 11E). Many of the untreated GL261 glioma-bearing mice were required to be euthanized as tumor volumes reached ~150 mm3 at the 21 day time-point.

Figure 13:
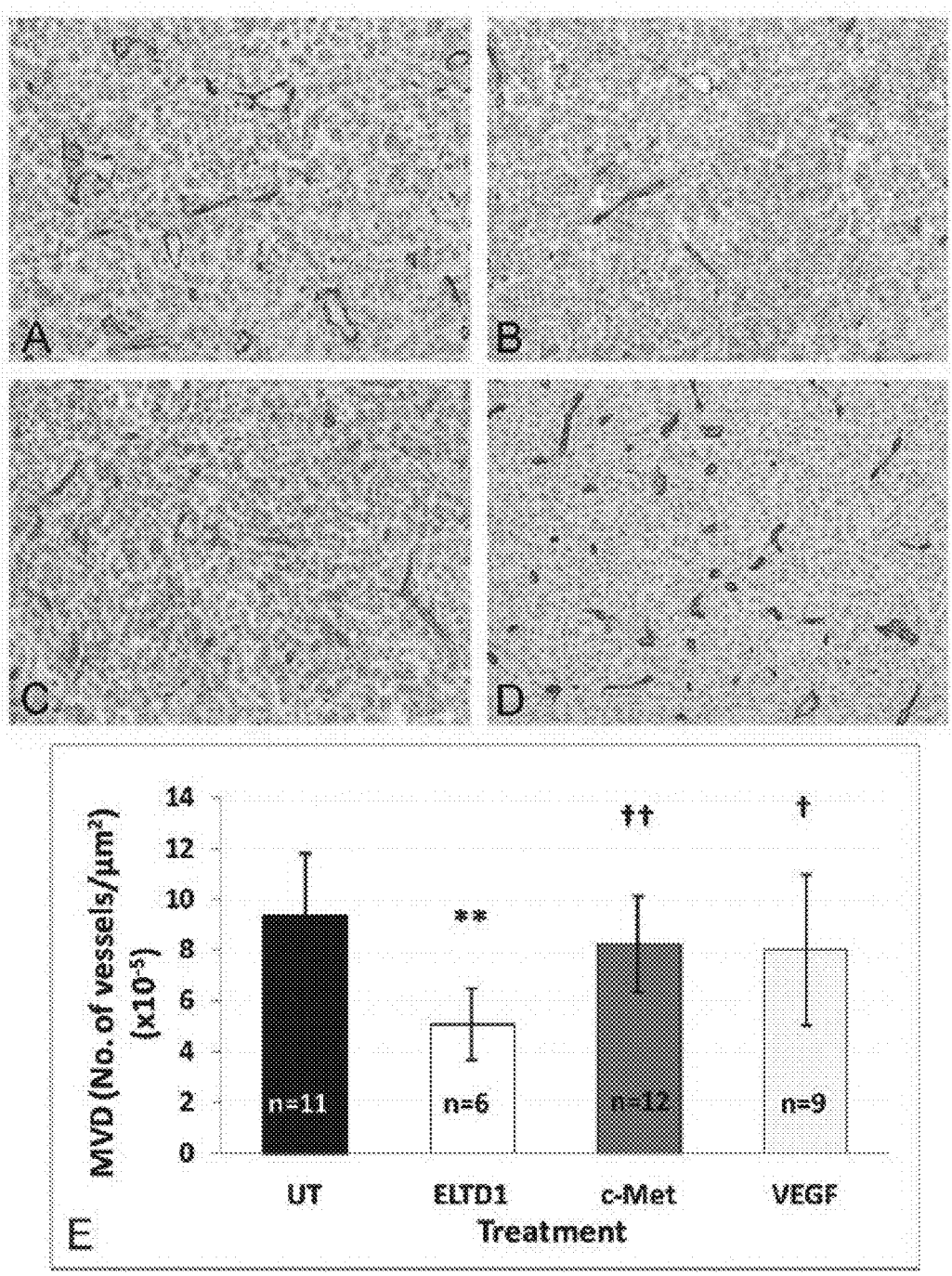
FIGS. 13A-E. Anti-ELTD1 antibody treatment decreases MVD in a mouse GL261 glioma model.
Figure 14:
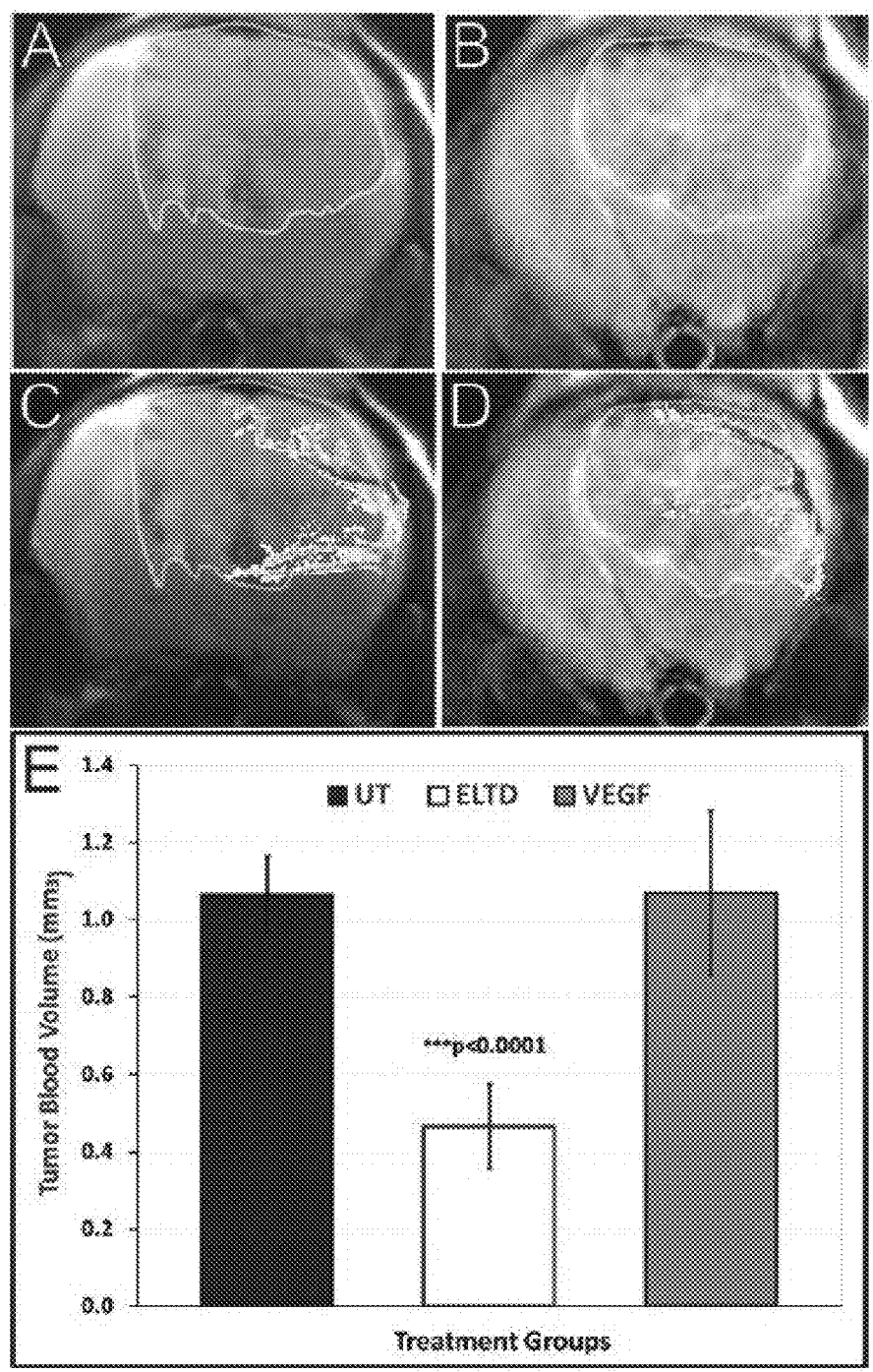
FIGS. 14A-E. Anti-ELTD1 antibody therapy decreases tumor blood volume in a mouse GL261 glioma model.
Figure 15:
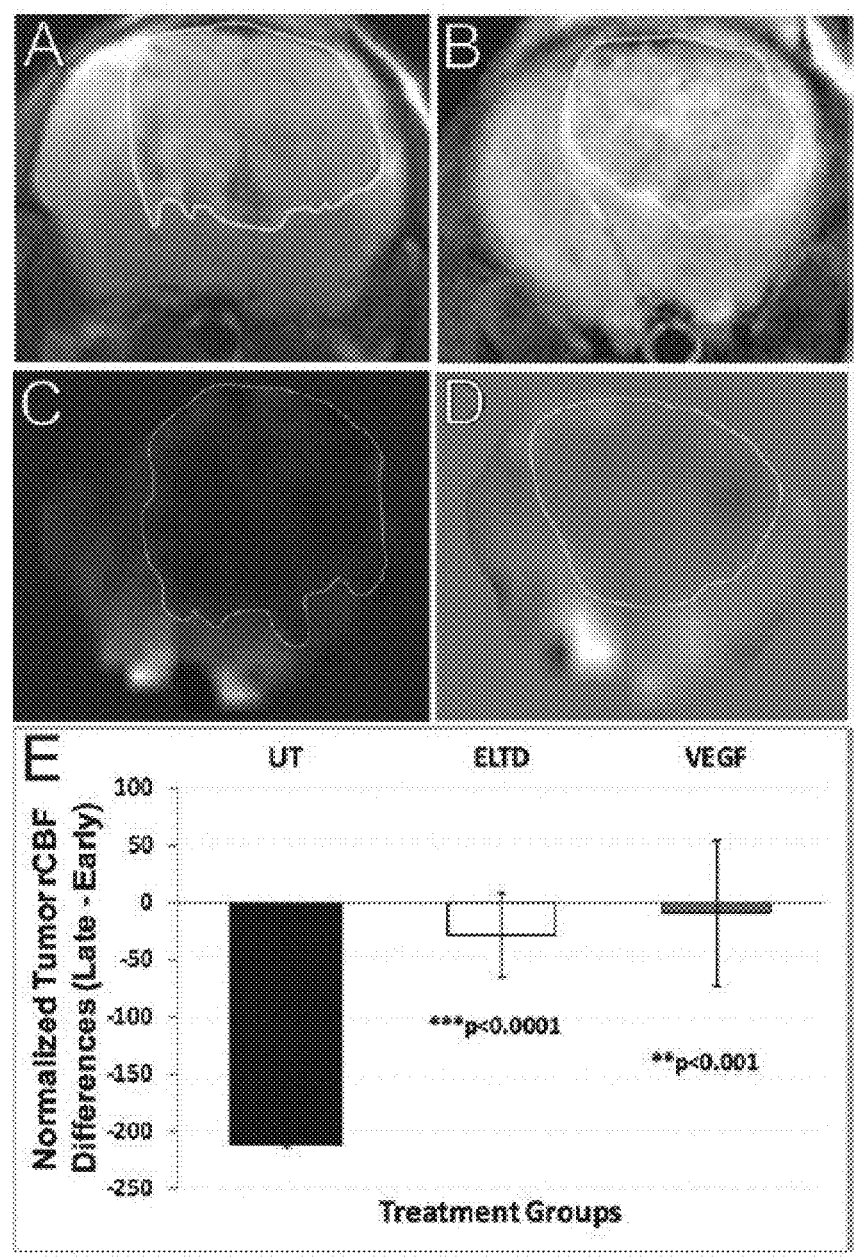
FIGS. 15A-E. Anti-ELTD1 antibody therapy alters tumor-associated vascularity as measured by MRI perfusion imaging.

Representative histological images for each treatment group are shown in FIGS. 12A-D. FIG. 12E depicts the quantitative histological assessment of the mitotic index of untreated and antibody (anti-ELTD1, anti-c-Met, anti-VEGF) treated groups. Both anti-ELTD1 and anti-c-Met antibody therapies were found to significantly decrease the mitotic index (p<0.05), compared to untreated mice. Representative CD-31 IHC images for each treatment group are shown in FIGS. 13A-D. Microvessel density (MVD) assessment for all treatment groups is shown in FIG. 13E, indicating that anti-ELTD1 antibody therapy significantly decreased MVD compared to untreated GL261 glioma-bearing mice (p<0.01). MVD was not significantly decreased for either anti-c-Met or anti-VEGF therapies. Anti-ELTD1 therapy was also found to be significantly lower than either anti-c-Met (p<0.01) or anti-VEGF (p<0.05) groups.

Representative morphological MR images and MR angiogram overlays of the brain regions from comparative untreated and anti-ELTD1 GL261 glioma-bearing mice are shown in FIGS. 14A-D. FIG. 14E illustrates the quantitative assessment of the tumor blood volumes (mm$_3$) that were calculated from MR angiograms obtained within brain regions of GL261 glioma-bearing mice that were either untreated, or treated with anti-ELTD1 or anti-VEGF antibody therapies. There was a significant decrease in total tumor blood volume in the anti-ELTD1 treatment group (p<0.0001) compared to the untreated group. Anti-VEGF therapy did not significantly decrease total tumor blood volume, when compared to untreated mice.

Representative morphological MR images and corresponding perfusion maps of brain regions from untreated and anti-ELTD1 GL261 glioma-bearing mice are shown in FIGS. 15A-D. The untreated mice had a characteristic decrease in rCBF in the tumor regions (see FIG. 15C), whereas the anti-ELTD1 treated mice had rCBF values that were similar to the contralateral brain (see FIG. 15D). FIG. 15E illustrates the quantitative assessment of the differences in tumor rCBF values, obtained between late and early tumor development and normalized to the contralateral region, that were calculated from MR perfusion maps obtained within brain regions of GL261 glioma-bearing mice that were either untreated, or treated with anti-ELTD1 or anti-VEGF antibody therapies. There was a significant decrease in the differences in rCBF values in both the anti-ELTD1 treatment group (p<0.0001) and the anti-VEGF treatment group (p<0.01), compared to the untreated group.

C. Discussion

Figure 9:
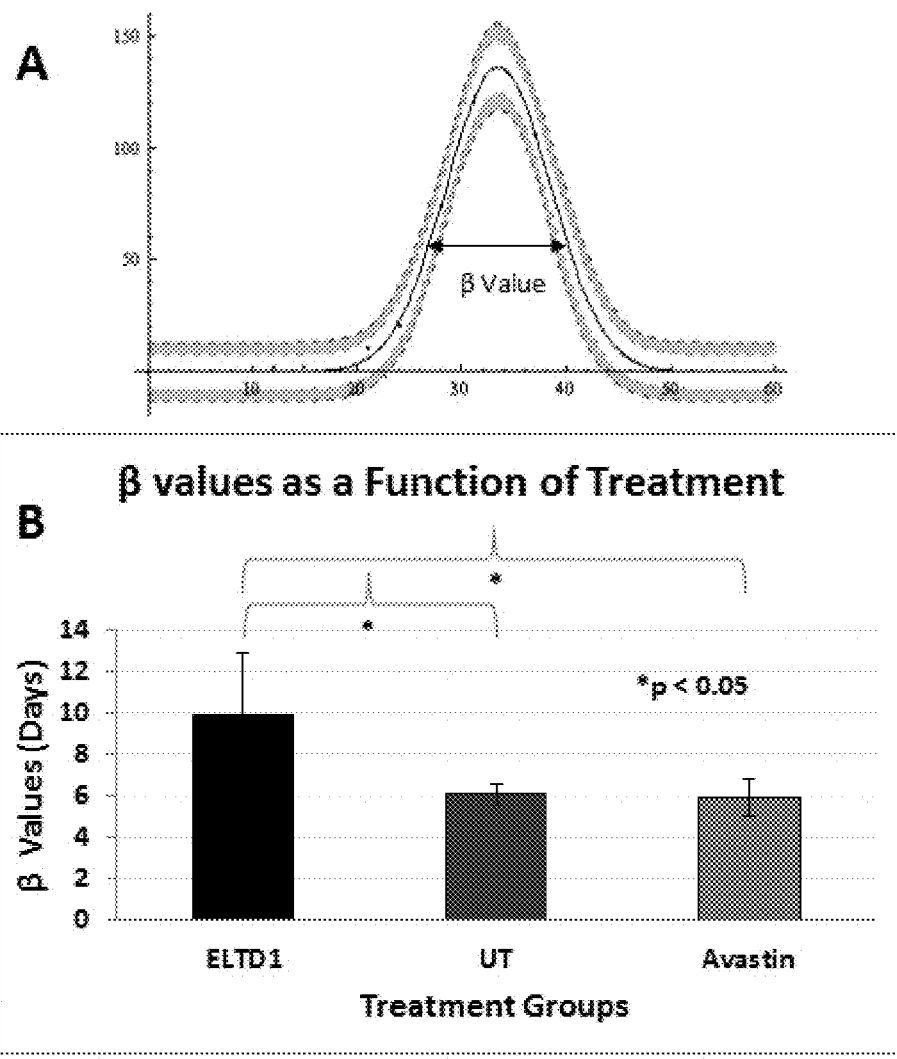
FIGS. 9A-B.
Figure 11:
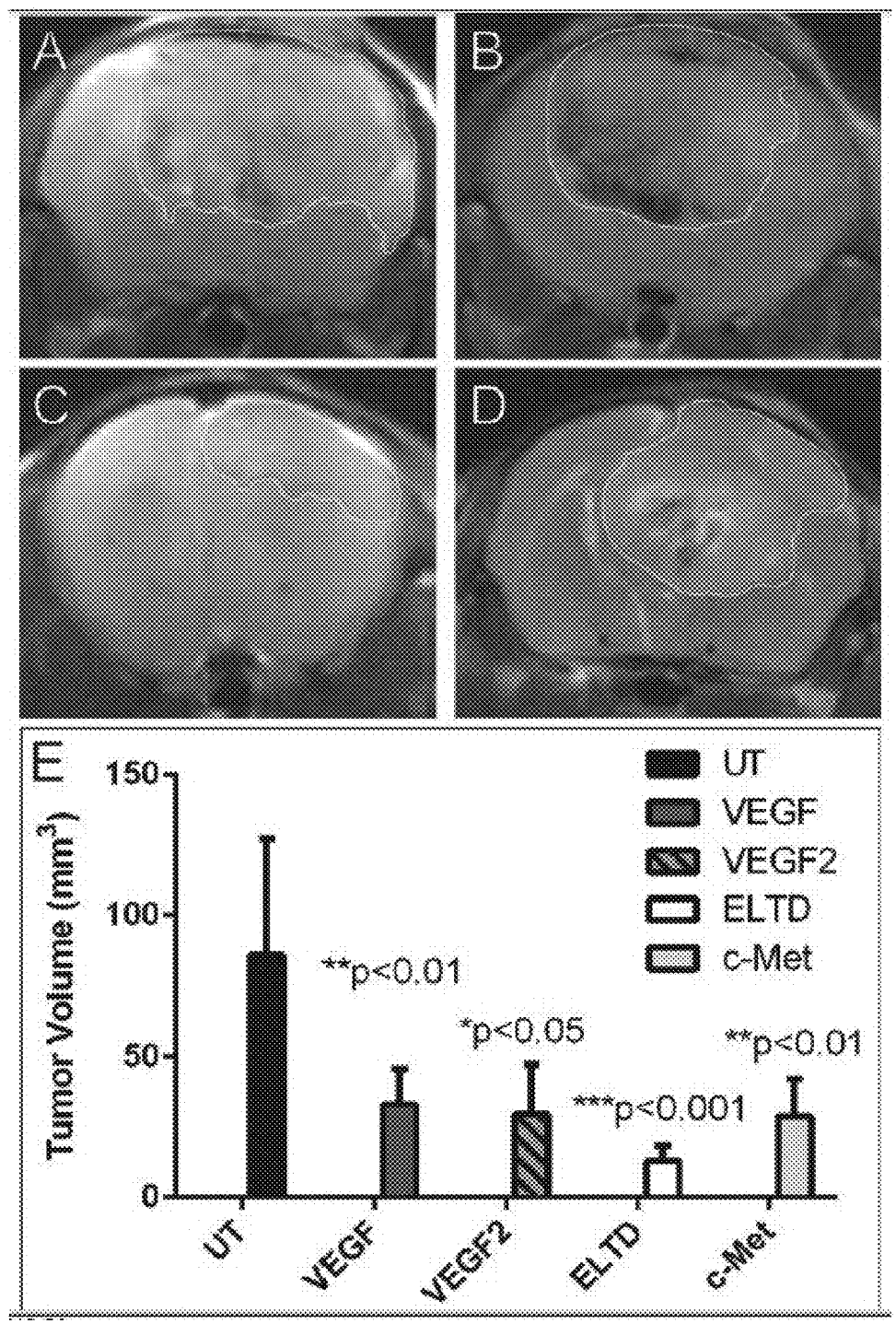
FIGS. 11A-E. Anti-ELTD1 antibody treatment decreases tumor volumes in a mouse GL261 glioma model.
Figure 12:
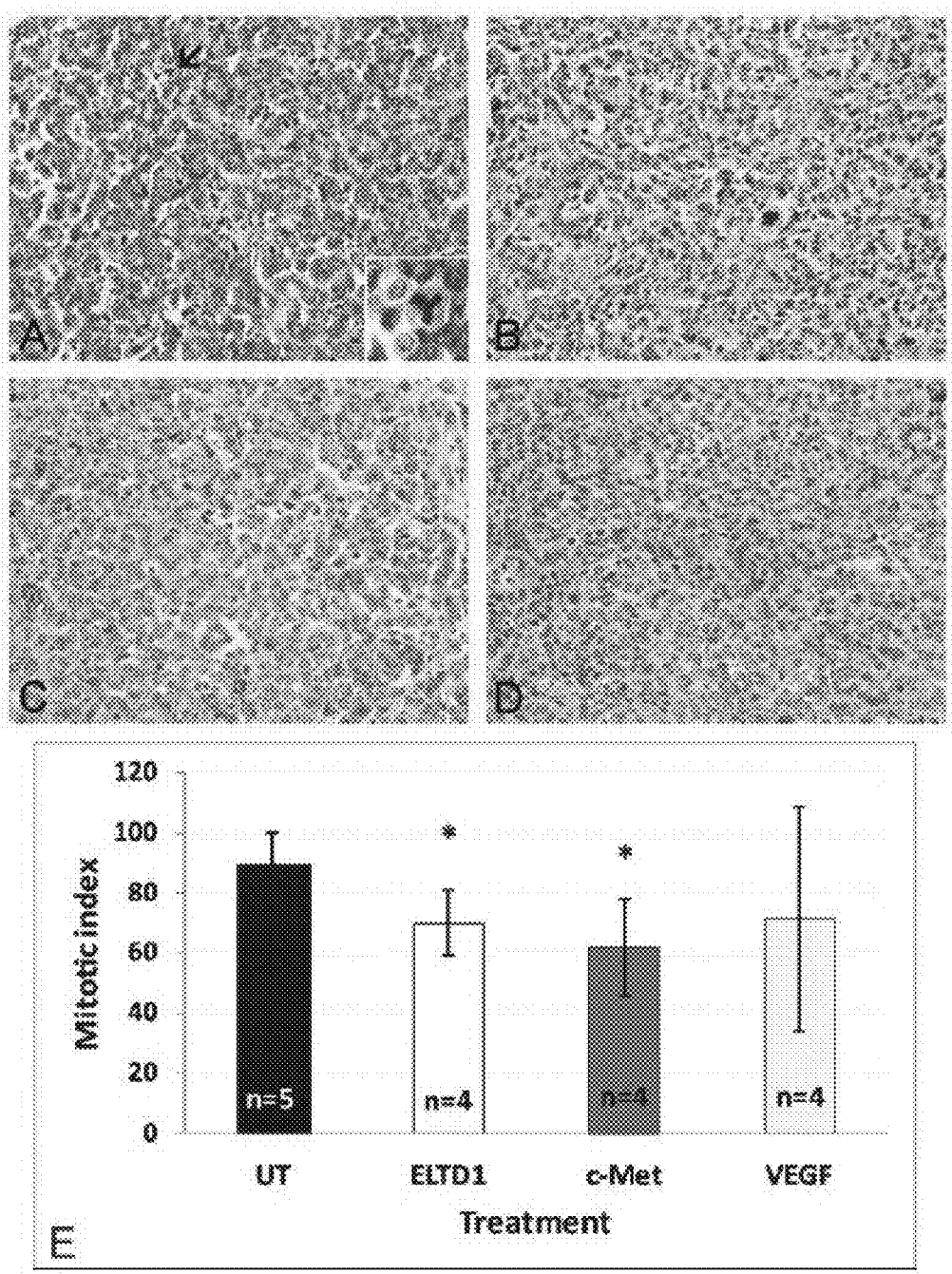
FIGS. 12A-E. Anti-ELTD1 antibody treatment decreases mitotic index in a mouse GL261 glioma model.

This study focuses on the observation that antibodies to ELTD1 inhibit the growth of mouse GL261 gliomas. These data show that multiple intravenous injections of anti-ELTD1 antibodies lead to a significant decrease in tumor volumes (FIGS. 9 and 10A-E), and an increase in animal survival (FIG. 9). Given a lifespan factor of 37.5 between mice and humans (Wu et al., 2013), the extra eight days in survival time gained by anti-ELTD1 therapy would translate into approximately a year for humans. Anti-ELTD1 therapy was found to significantly decrease the mitotic index, compared to untreated tumors (FIG. 11). Furthermore, the magnitude of the effect is superior to that achieved by a mouse anti-VEGF antibody, similar to the humanized version bevacizumab (Avastin), a commercial FDA-approved angiogenesis inhibitor. In particular, anti-ELTD1 therapy was found to significantly decrease MVD compared to untreated tumors (FIGS. 12A-E), whereas anti-VEGF therapy did not significantly affect MVD. With the use of MR angiography and dynamic contrast enhanced (DCE)-MRI by other investigators it was determined that bevacizumab/paclitaxel combined therapy did not block the blood supply to a MCF-7 breast tumor xenograft in SCID mice, which diminished any microvascular changes targeted by the anti-VEGF antibody therapy (Zhu et al., 2014). This finding is consistent with the modest survival benefits of adding bevacizumab to current treatment regimens for some types of cancers (Zhu et al., 2014), such as gliomas (Beal et al., 2011 and Vredenburgh et al., 2011). The inventors' bioinformatics analysis suggests ELTD1 is induced in angioblasts, regions of neovascularization, and not in normal tissue (Towner et al., 2013), further indicating that this molecular target may be ideal for anti-angiogenic therapy. A recent report by Masiero et al. (2013) also supports the inventors' data that ELTD1 is a key regulator of angiogenesis (Masiero et al., 2013). MR angiography and MR perfusion imaging indicated that ELTD1 was able to decrease the tumor blood vasculature (blood vessels >50 μm in diameter) (see FIGS. 14A-E) and differences in tumor rCBF values (see FIGS. 15A-E), respectively. Anti-ELTD1 antibody therapy seems to affect both macro- and micro-vasculature associated with tumor growth, whereas in this study anti-VEGF antibody therapy only seems to affect tumor microvasculature. The MVD data seems to also support this finding as MVD takes into consideration both macro- and micro-vasculature measurements. Perhaps anti-ELTD1 therapy can be used as an alternate anti-angiogenic therapy clinically. Anti-ELTD1 antibody therapy may also be considered to be used in combination with anti-c-Met therapy in future studies. These data, in addition to other independent reports recently published (Dieterich et al., 2012), suggests that ELTD1 is a promising therapeutic candidate for inhibition of angiogenesis in gliomas, and quite possibly in other tumors as well.

Example 3

Plexin-B2, Spondin-1 and Slit3 as Therapeutic Targets

Plexin-B2. Anti-Plexin-B2 antibody therapy was found to significantly increase animal survival (FIG. 16) and significantly decrease tumor volumes (FIGS. 17A-C) in a mouse GL261 glioma model, when compared to untreated tumor-bearing controls.

Spondin-1. Anti-Spondin-1 antibody therapy was found to significantly increase animal survival (FIG. 18) and significantly decrease tumor volumes (FIGS. 19A-C) in a mouse GL261 glioma model, when compared to untreated tumor-bearing controls.

Figure 20:
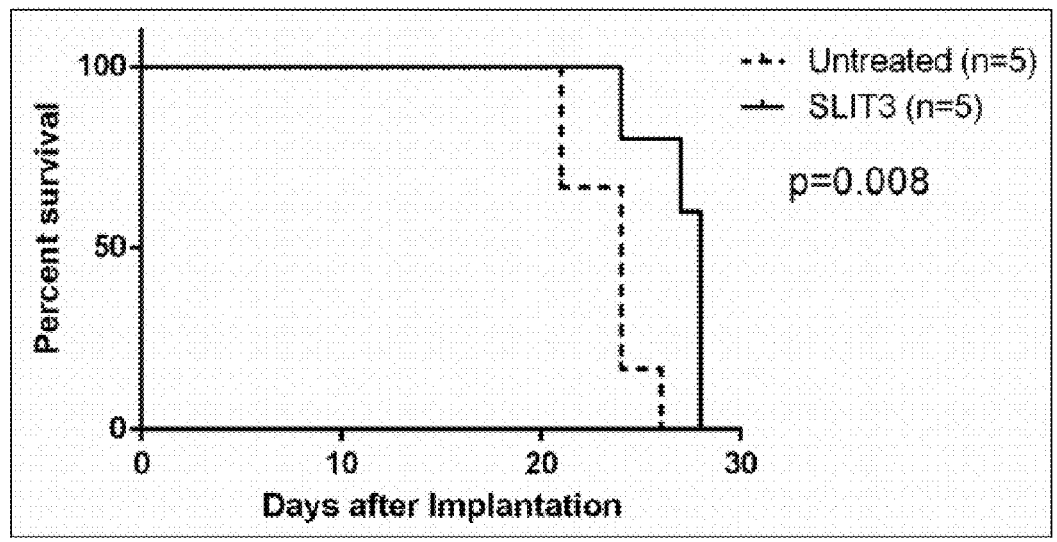
FIG. 20. Anti-SLIT3 antibody therapy increases animal survival in a GL261 mouse glioma model. Animal survival curves for GL261 glioma-bearing mice either untreated (UT) (n=5), or treated with an antibody against SLIT3 (n=5). There was a significant increase in survival for the treated group ($p<0.05$), compared to untreated mice.
Figure 21:
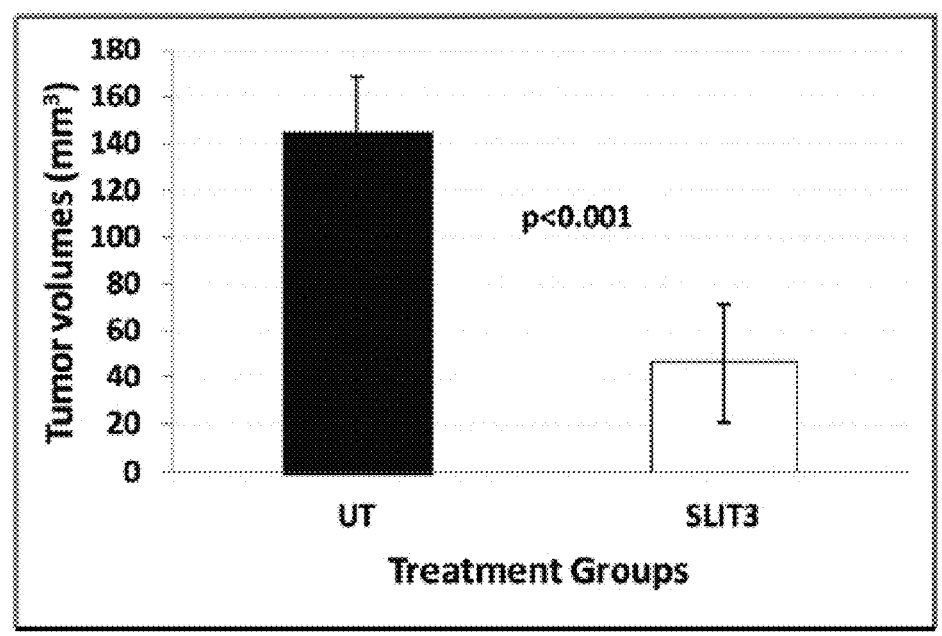
FIG. 21. Anti-SLIT3 antibody treatment decreases tumor volumes in a mouse GL261 glioma model. Histogram depicting tumor volumes (mm3), as measured from multiple MR image slices for either GL261 glioma mice that were untreated (UT) or treated with an antibody against SLIT3. There was a significant decrease in tumor volumes for the treated group ($p<0.001$) compared to UT animals.

SLIT3. Anti-SLIT3 antibody therapy was found to significantly increase animal survival (FIG. 20) and significantly decrease tumor volumes (FIGS. 21A-C) in a mouse GL261 glioma model, when compared to untreated tumor-bearing controls.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,680,338
U.S. Pat. No. 4,683,202
U.S. Pat. No. 4,684,611
U.S. Pat. No. 4,816,567
U.S. Pat. No. 4,867,973
U.S. Pat. No. 4,938,948
U.S. Pat. No. 4,952,500
U.S. Pat. No. 5,021,236
U.S. Pat. No. 5,141,648
U.S. Pat. No. 5,196,066
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,563,250
U.S. Pat. No. 5,565,332
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,780,448
U.S. Pat. No. 5,789,215
U.S. Pat. No. 5,824,544
U.S. Pat. No. 5,856,456
U.S. Pat. No. 5,880,270
U.S. Pat. No. 5,945,100
U.S. Pat. No. 5,981,274
U.S. Pat. No. 5,994,624
"Antibodies: A Laboratory Manual," Cold Spring Harbor Press, Cold Spring Harbor, N.Y., 1988.
Abbondanzo et al., *Am. J. Pediatr. Hematol. Oncol.*, 12(4), 480-489, 1990.
Agrawal and Lynskey, *Addiction*, 104: 518-32, 2009.
Agrawal et al., *Arch Gen Psychiatry*, 65: 713-21, 2008.
Allred et al., *Arch. Surg.*, 125(1), 107-113, 1990.
Argast et al., Oncogene, 28:2697-709, 2009.
Atherton et al., *Biol. of Reproduction*, 32, 155-171, 1985.
Ausubel et al., *Current Protocols in Molecular Biology*, Greene Publishing Associates and Wiley Interscience, N.Y., 1994.
Basile et al., Cancer Res 64:5212-24, 2004.
Beal et al., Radiat Oncol, 6: 2. PMCID:PMC3025871, 2011.
Beidler et al., *J Immunol.*, 141(11):4053-4060, 1988.
Brown et al., *J. Immunol. Meth.*, 12; 130(1), :111-121, 1990.
Capaldi et al., *Biochem. Biophys. Res. Comm.*, 74(2):425-433, 1977.
Chen and Okayama, *Mol. Cell Biol.*, 7(8):2745-2752, 1987.
Cheng et al., *Br J Cancer*, 99:2083-7, 2008.
Chillon et al., *J. Virol.*, 73(3):2537-2540, 1999.
Conrotto et al., *Oncogene*, 23:5131-7, 2004.
Culotta and Hamer, *Mol. Cell. Biol.*, 9:1376-1380, 1989.
D'Halluin et al., *Plant Cell*, 4(12):1495-1505, 1992.
Dandolo et al., *J. Virology*, 47:55-64, 1983.
Davidson et al., *J Cell Mol Med*, 15:535-44, 2011.
De Jager et al., *Semin. Nucl. Med.* 23(2), 165-179, 1993.
Dholakia et al., *J. Biol. Chem.*, 264, 20638-20642, 1989.
Dickinson et al., *Br J Cancer*, 91:2071-8, 2004.
Dieterich et al., J Pathol, 228:378-90, 2012.
Doblas et al., J Magnetic Resonance Imaging, 32:267-75, 2010.
Doolittle and Ben-Zeev, *Methods Mol. Biol.*, 109, :215-237, 1999.
EP Application 125,023
EP Application 171,496
EP Application 173,494

EP Application 184,187
Fechheimer et al., *Proc Natl. Acad. Sci. USA*, 84:8463-8467, 1987.
Flynn et al., *Cancer*, 113:1032-42, 2008.
Fraley et al., *Proc. Natl. Acad. Sci. USA*, 76:3348-3352, 1979.
Garteiser et al., J Magn Reson Imaging, 31:796-806, 2010.
Gefter et al., *Somatic Cell Genet.*, 3:231-236, 1977.
Giles and Wren, *BMC Bioinformatics*, 9 Suppl 9:S11, 2008.
Gillespie et al., *Clin Cancer Res*, 13:2441-8, 2007.
Gillespie et al., *Methods Mol Biol*, 487:283-301, 2009.
Goding, In: *Monoclonal Antibodies: Principles and Practice*, 2d ed., Orlando, Fla., Academic Press, 60-61, 65-66, 71-74, 1986.
Gopal, *Mol. Cell Biol.*, 5:1188-1190, 1985.
Graham and Van Der Eb, *Virology*, 52:456-467, 1973.
Gulbis and Galand, *Hum. Pathol.* 24(12), 1271-1285, 1993.
Gyorffy et al., *Int J Gynecol Cancer*, 18:1215-33, 2008.
Harland and Weintraub, *J Cell Biol.*, 101(3):1094-1099, 1985.
Herscovitch et al., J Cereb Blood Flow Metab, 5:65-69, 1985.
Holl et al., *PLoS One.*, 7:e43333, 2012.
Imai et al., *Nephrologie*, 19(7):397-402, 1998.
Jensen et al., *J Neurooncol*, 78:233-47, 2006.
Jensen, *Neurosurg Focus*, 20(4):E24, 2006.
Jones et al., *Nature*, 321:522-525, 1986.
Kadesch and Berg, *Mol. Cell. Biol.*, 6:2593, 1986.
Kanda et al., *Mol Carcinog*, 50:571-9, 2011.
Kaneda et al., *Science*, 243:375-378, 1989.
Kato et al, *J Biol. Chem.*, 266:3361-3364, 1991.
Katoh and Katoh, Oncol Rep, 14:1351-5, 2005.
Katoh et al., *Oncol Rep.*, 14:1351-5, 2005.
Khatoon et al., *Ann. of Neurology*, 26, 210-219, 1989.
King et al., *J. Biol. Chem.*, 269, 10210-10218, 1989.
Kobel et al., *PLoS Med*, 5:e232, 2008.
Kohler and Milstein, *Eur. J Immunol.*, 6, 511-519, 1976.
Kohler and Milstein, *Nature*, 256, 495-497, 1975.
Lazzeri, *Methods Mol. Biol.*, 49:95-106, 1995.
Lee et al., *PLoS One*, 6: e16356, 2011.
Lin and Chuang, *Biomed Pharmacother*, 66:454-8, 2012.
Loov et al., *PLoS One*, 7:e29771, 2012.
Masiero et al., Cancer Cell, 24:229-41, 2013.
Medioni et al., Dev Dyn, 239:3303-11, 2010.
Morrison, *Science*, 229(4719):1202-1207, 1985.
Nakamura et al., In: *Enzyme Immunoassays: Heterogeneous and Homogeneous Systems*, Chapter 27, 1987.
Nechiporuk et al., *J Biol Chem*, 276: 4150-7, 2001.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-428, 1993.
O'Shannessy et al., *J. Immun. Meth.*, 99, 153-161, 1987.
PCT Application PCT/US86/02269
PCT Application WO 86/01533
PCT Appln. WO 92/17598
PCT Appln. WO 94/09699
Pepinsky et al., *J Pharmacol Exp Ther*, 339:519-29, 2011.
Pepinsky, et al., J Pharmacol Exp Ther, 339:519-29, 2011.
Phillips et al., *Cancer Cell*, 9:157-73, 2006.
Porto Neto et al., *Anim Genet*, 42: 50-5, 2011.
Posner et al., *Hybridoma* 6, 611-625, 1987.
Potrykus et al., *Mol. Gen. Genet.*, 199(2):169-177, 1985.
Potter and Haley, *Meth. Enzymol.*, 91, 613-633, 1983.
Pupa et al., *Oncogene*, 23:2153-60, 2004.
Pyle-Chenault et al., *Tumour Biol*, 26:245-57, 2005.
Ragel et al., *Neurosurg Rev.*, 30:181-7; discussion 7, 2007.
Rippe, et al., *Mol. Cell Biol.*, 10:689-695, 1990.
Robbins and Ghivizzani, *Pharmacol Ther*, 80(1):35-47, 1998.
Robbins et al., *Trends Biotechnol.*, 16(1):35-40, 1998.
Roney et al., *PLoS One.*, 6:e24795, 2011.
Rong et al., *Cancer Res.*, 66:7067-74, 2006.
Sambrook et al., In: *Molecular cloning: a laboratory manual*, $2^{nd}$ Ed., Cold Spring Harbor Laboratory Press, Cold Spring Harbor, N.Y., 1989.
Shaw et al., *J. Natl. Cancer Inst.*, 80(19):1553-1559, 1988.
Stein et al., *Neurosci Lett*, 509:9-12, 2012.
Sun et al., *J. Steroid Biochem.*, 26(1):83-92, 1987.
Towner et al., Neuro Oncol, 15:1625-34, 2013.
Towner et al., Neurosurgery, January; 72: 77-91. PMCID: PMC3555701, 2013.
Verhaak et al., *Cancer Cell*, 17:98-110, 2010.
Verhoeyen et al., *Science*, 239(4847):1534-1536, 1988.
Vredenburgh et al., Clin Cancer Res, 17(12): p. 4119-24, 2011.
Wawrzynczak & Thorpe, *Cancer Treat Res.*, 37:239-51, 1988.
Wen et al., *Clin Cancer Res*, 12:5951-9, 2006.
Wen et al., *J. Biol. Chem.*, 278:38029-38039, 2003.
Wlazlinski et al., *Prostate*, 67:1770-80, 2007.
Wong et al., *Gene*, 10:87-94, 1980.
Wood et al., *J. Clin. Lab. Immunol.*, 17(4):167-171, 1985.
Wren, *Bioinformatics*, 20:191-8, 2004.
Wren, *Bioinformatics*, 25:1694-701, 2009.
Wren, BMC Bioinformatics, 5:145, 2004.
Wu et al., Cell Rep, 4(5):p. 913-920, 2013.
Zhang et al., J Biol Chem, 284:15717-28, 2009.
Zhu et al., Plos One, 9:e86583, 2014.

The invention claimed is:

1. A method of inhibiting a glioma cell comprising contacting said glioma cell with a first antibody or antibody fragment that binds immunologically to ELTD1, Spondin-1 or SLIT3.

2. The method of claim 1, further comprising contacting said glioma cell with a second anti-cancer agent or treatment.

3. The method of claim 2, wherein said second anti-cancer agent or treatment is selected from chemotherapy, radiotherapy, immunotherapy, hormonal therapy, or toxin therapy.

4. The method of claim 2, wherein said second anti-cancer agent or treatment is given at the same time as said first antibody or antibody fragment.

5. The method of claim 2, wherein said second anti-cancer agent or treatment is given before and/or after said first antibody or antibody fragment.

6. The method of claim 1, wherein said glioma cell is a metastatic glioma cell, a multiply drug resistant glioma cell or a recurrent glioma cell.

7. The method of claim 1, wherein said first antibody or antibody fragment is a single chain antibody or antibody fragment.

8. The method of claim 1, wherein said first antibody or antibody fragment is a chimeric antibody a Fab fragment, or a murine antibody or antibody fragment.

9. The method of claim 1, wherein said first antibody is an IgG, a humanized antibody, or a humanized IgG antibody.

10. The method of claim 1, wherein said first antibody or antibody fragment further comprises an antitumor drug or label linked thereto.

11. The method of claim 10, wherein said antitumor drug is linked to said first antibody or antibody fragment through a photolabile linker, or through an enzymatically-cleaved linker.

12. The method of claim 10, wherein said antitumor drug is a toxin, a radioisotope, a cytokine, or an enzyme.

13. The method of claim 10, wherein said label is a peptide tag, an enzyme, a magnetic particle, a chromophore, a fluorescent molecule, a chemilluminescent molecule, or a dye.

14. The method of claim 1, wherein said first antibody or antibody fragment is conjugated to a liposome or nanoparticle.

15. The method of claim 1, wherein said first antibody or antibody fragment results in the induction of cell death.

16. The method of claim 2, wherein said second agent is an anti-VEGF antibody, an anti-EGFR antibody or an anti-c-Met antibody.

17. The method of claim 2, wherein said second agent is a second anti-ELTD1 antibody, anti-Spondin-1 antibody or anti-SLIT3 antibody distinct first antibody or antibody fragment.

18. A method of treating glioma in a subject comprising administering to said subject a first antibody or antibody fragment that binds immunologically to ELTD1, Spondin-1 or SLIT3.

19. The method of claim 15, wherein the induction of cell death involves antibody-dependent cell cytotoxicity or complement-mediated cytotoxicity.

* * * * *